US009228949B2

(12) United States Patent
Tang et al.

(10) Patent No.: US 9,228,949 B2
(45) Date of Patent: Jan. 5, 2016

(54) AGGREGATION-INDUCED EMISSION LUMINOGENS FOR METAL ION DETECTION

(75) Inventors: Benzhong Tang, Hong Kong (CN); Yuning Hong, Hong Kong (CN); Wai Tung Leung, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 532 days.

(21) Appl. No.: 13/602,641

(22) Filed: Sep. 4, 2012

(65) Prior Publication Data
US 2013/0059392 A1 Mar. 7, 2013

Related U.S. Application Data

(60) Provisional application No. 61/573,115, filed on Sep. 6, 2011.

(51) Int. Cl.
*G01N 21/64* (2006.01)
*G01N 31/22* (2006.01)
(Continued)

(52) U.S. Cl.
CPC .......... *G01N 21/643* (2013.01); *G01N 21/3103* (2013.01); *G01N 31/22* (2013.01);
(Continued)

(58) Field of Classification Search
CPC ... G01N 31/22; G01N 33/20; G01N 33/1813; G01N 33/0045; G01N 21/3103; G01N 33/84; C02F 1/72; C02F 11/086; A61K 31/295; A61K 31/7016; A61K 33/26
USPC ................................................ 436/80, 81, 84
See application file for complete search history.

(56) References Cited

U.S. PATENT DOCUMENTS 7,105,680 B1 9/2006 O'Halloran et al.
7,456,023 B2 11/2008 Klimant
(Continued)

OTHER PUBLICATIONS

Fluorogenic Zn(II) and Chromogenic Fe(II) Sensors Based on Terpyridine-Substituted Tetraphenylethenes with Aggregarion-Induced Emission Characteristics Yuning Hong, Sijie Chen, Chris Wai Tung Leung, Jacky Wing Yip Lam, Jianzhao Liu, Nai-Wen Tseng, Ryan Tsz Kin Kwok, Yong Yu, Zhengke Wang, Ben Zhong Tang, ACS Appl. Mater. Interfaces 2011, 3, 3411-3418.*
(Continued)

*Primary Examiner* — Krishnan S Menon
*Assistant Examiner* — Dwan A Gerido
(74) *Attorney, Agent, or Firm* — Nath, Goldberg & Meyer; Joshua B. Goldberg; Christopher Thomas

(57) ABSTRACT

Pyridine-containing polyenes and their applications as metal ion sensors. These polyenes are practically nonluminescent in the solution state but become highly emissive as nanoparticle suspensions in aqueous solutions or thin films in the solid state, due to aggregation-induced emission (AIE). The nano-aggregates of these compounds can work as "turn-off" fluorescent chemosensors for metal ions and display different fluorescence responses to various metal ions. For example, a characteristic red shift in the emission spectra is observed with a terpyridine-containing luminogen in the presence of $Zn^{2+}$. However, the terpyridine-containing luminogen displays a magenta color upon selectively binding with $Fe^{2+}$. This allows easy identification of both $Zn^{2+}$ and $Fe^{2+}$ ions in aqueous media. The function of the polyenes can be easily tuned by altering the substituent groups. Due to their AIE properties, these polyenes can be used in aqueous solutions and in solid substrates for metal sensing.

14 Claims, 12 Drawing Sheets

(51) Int. Cl.
- *G01N 33/20* (2006.01)
- *G01N 33/18* (2006.01)
- *G01N 33/00* (2006.01)
- *G01N 21/31* (2006.01)
- *G01N 33/84* (2006.01)

(52) U.S. Cl.
CPC ........ *G01N33/0045* (2013.01); *G01N 33/1813* (2013.01); *G01N 33/20* (2013.01); *G01N 33/84* (2013.01); *G01N 2021/6417* (2013.01)

(56) References Cited

U.S. PATENT DOCUMENTS

| | | | |
|---|---|---|---|
| 7,541,467 B2 | 6/2009 | Yano et al. | |
| 7,696,245 B2 | 4/2010 | Komatsu et al. | |
| 2008/0220407 A1* | 9/2008 | Tang et al. | 435/4 |
| 2010/0009362 A1* | 1/2010 | Tang et al. | 435/6 |
| 2011/0065195 A1 | 3/2011 | Tew et al. | |

OTHER PUBLICATIONS

A new ligand and its complex with multi-stimuli-responsive and aggregation induced emission effects Bingjia Xu, Zhenguo Chi, Xiqi Zhang, Haiyin Li, Chengjian Chen, Siwei Liu, Yi Zhang, and Jiarui Xu Chem. Commun., 2011, 47, 11080-11082.*

Terpyridine Based Cruciform Zn2+ Complexes as Anion Responsive Fluorophores Scott M. Brombosz, Anthony J. Zucchero, Ronnie L. Phillips, Diana VAzquez, Alando Wilson, and Uwe H.F. Bunz Organic Letters, 2007, vol. 9, No. 22, 4519-4522.*

Manipulating Localized Molecular Orbitals by Single Atom Contacts Weihua Wang, Xingquang Shi, Chensheng Lin, Rui Qin Zhang, Christian Minot, Michel A. Van Hove, Yuning Hong, Ben Zhong Tang, and Nian Lin Physical Review Letters 105, 126801, 2010.*

Manipulating Localized Molecular Orbitals by Single-Atom Contacts Weihua Wang, Xingqiang Shi, Chensheng Lin, Rui Qin Zhang, Christian Minot, Michel A. Van Hove, Yuning Hong, BenZhong Tang, and Nian Lin Physical Review Letters 105, 2010.*

Bingjia Xu, et al., "A new ligand and its complex with multi-stimuli-responsive and aggregation-induced emission effects", Chem. Commun., 2011, 47, pp. 11080-11082.

Valentina Spampinato, et al., "Functionalization of Oxide Surfaces by Terpyridine Phosphonate Ligands: Surface Reactions and Anchoring Geometry", Langmuir, 2010, 26 (11), pp. 8400-8406.

Rudrakanta Satapathy, et al., "Novel Thieno-imidazole Based Probe for Colorimetric Detection of Hg2+ and Fluorescence Turn-on Response of Zn2+", Organic Letters, 2012, vol. 14, No. 10, pp. 2564-2567.

Claudia Haensch, et al., "Reversible Supramolecular Functionalization of Surfaces: Terpyridine Ligands as Versatile Building Blocks for Noncovalent Architectures", Langmuir, 2008, 24, pp. 12981-12985.

Florian Schlutter, et al., "Synthesis and Characterization of New Self-Assembled Metallo-Polymers Containing Electron-Withdrawing and Electron-Donating Bis(terpyridine)Zinc(II) Moieties", Macromolecules, 2010, 43, pp. 2759-2771.

Scott M. Brombosz, et al., "Terpyridine-Based Cruciform-Zn2+ Complexes as Anion-Responsive Flurophores", Organic Letters, 2007, vol. 9, No. 22, pp. 4519-4522.

Guntram Schwarz, et al., "The structure of metallo-supramolecular polyelectrolytes in solution and on surfaces", Journal of Materials Chemistry, 2010, 20, p. 4142-4189.

* cited by examiner

AGGREGATION-INDUCED EMISSION LUMINOGENS FOR METAL ION DETECTION

RELATED APPLICATIONS

The present patent application claims priority to Provisional Patent Application No. 61/573,115, filed Sep. 6, 2011, which is assigned to the assignee hereof and filed by the inventors hereof and which is incorporated by reference herein.

TECHNICAL FIELD

The present subject matter relates to a compound or salt thereof that can be used as a highly selective fluorescent metal ion sensor.

BACKGROUND

Zinc is an essential trace element necessary for plants, animals, and microorganisms. It is the second most abundant transition metal in the human body after iron. Zinc is one of the most important cations in catalytic centers and structural cofactors of many enzymes and metalloproteins. It is an essential factor in many biological processes such as the metabolism of DNA and RNA, sign transduction, and gene expression, as well as the pathological processes in many diseases including Alzheimer's disease, epilepsy, and ischemic stroke.

In blood plasma, zinc is bound to and transported by albumin and transferrin. Since transferrin also transport iron, an excessive amount of zinc will result in insufficient absorption of iron. Although most zinc ions are tightly bound to enzymes and proteins, the physiological roles of free zinc pools in certain tissues have yet to be explored. Unlike other biological transition metal ions such as $Fe^{2+}$ and $Cu^{2+}$, $Zn^{2+}$ is spectroscopically and magnetically silent due to its d10 electron configuration. As a result, sensitive and non-invasive fluorescence-based techniques are ideal for zinc analysis and imaging.

However, most of the fluorescent zinc sensors disclosed in the prior art are based on conventional organic luminophores, such as O'Halloran et al. (U.S. Pat. No. 7,105,680), Komatsu (U.S. Pat. No. 7,696,245), Yano et al. (U.S. Pat. No. 7,541,467), and Nagano et al. (U.S. Pat. No. 6,903,226). Most of these probes were constructed based on Rhodamine or fluorescein derivatives. These conventional organic luminophores exhibit high fluorescence in dilute solutions, but suffer from aggregation-caused quenching (ACQ) in the condensed or solid phase. When dispersed in aqueous media or fabricated into solid film, the fluorescence of conventional luminophores is often weakened or even quenched, which greatly limits their real-world applications.

Likewise, most terpyridine based metal ion sensors reported in the literature are only used in organic solvents or mixed solvents with high fractions of organic solvents. This is because these fluorophores undergo aggregation-caused self-quenching when dispersed in the aqueous media. This problem is more severe in the solid state. However, fluorophores with aggregation-induced emission (AIE) properties can overcome this problem. They are stable in water and resistant to self-quenching upon aggregation.

To make the fluorescence cation sensors work in aqueous solution, bulky alicyclics and dendritic wedges are attached to aromatic rings to obstruct the formation of aggregates. Despite the nontrivial synthetic effort, these approaches often result in undesired side effects. Still, for most organic dyes, it is difficult to distinguish $Zn^{2+}$ from other metal species, including its analogue $Cd^{2+}$. It is also difficult to distinguish $Fe^{2+}$ from $Fe^{3+}$.

Accordingly, there is a great need for the development of fluorescent sensors for metal ions with high selectivity and superior practical use, including the ability to be easily tuned by altering substituent groups and easy synthesis thereof.

SUMMARY

In view of the foregoing, an object of the present subject matter is to provide a compound or salt thereof exhibiting aggregation-induced emission properties, that can be used as a highly selective fluorescent sensor for metal ions, thereby overcoming various deficiencies and shortcomings of the prior art. More specifically, an object of the present subject matter is to provide a compound or salt thereof that can specifically capture a metal ion in a complex, wherein the complex after the capture has a superior fluorescent characteristic. In addition, another object of the present subject matter is to provide a method for detecting and identifying a metal ion using the highly selective fluorescent sensor for metal ions.

It is an object of the present subject matter to provide a fluorescent sensor for metal ions comprising a luminogen that exhibits aggregation-induced emission properties functionalized with a terpyridine moiety; wherein the luminogen functionalized with terpyridine moiety comprises a backbone structure selected from the group consisting of:

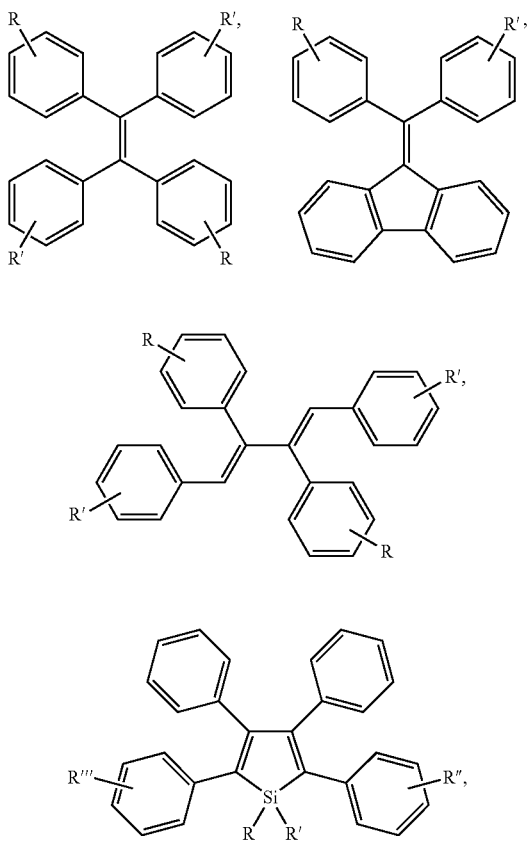

-continued
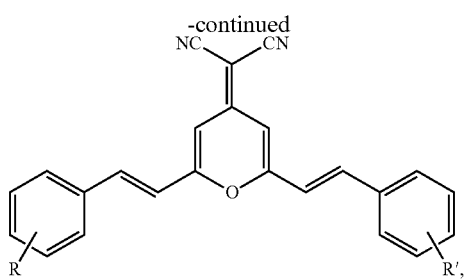
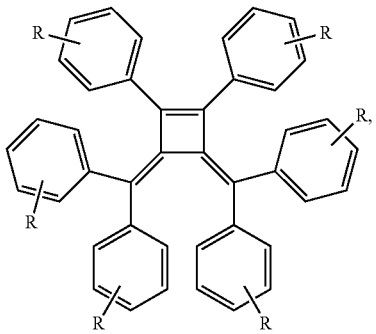
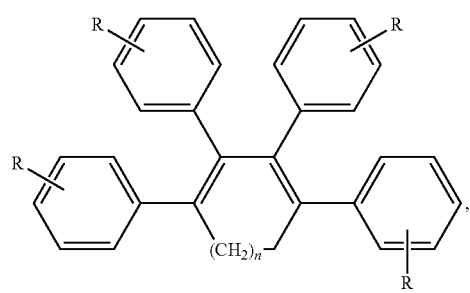
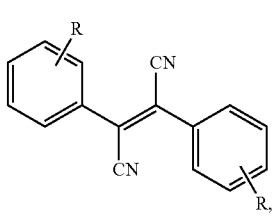 and
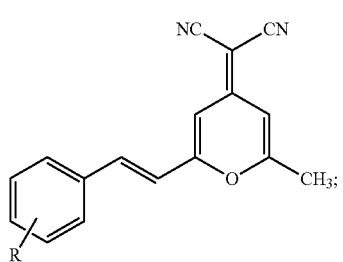
wherein R and R' are independently selected from the group consisting of H, alkyl, unsaturated alkyl, heteroalkyl, cycloalkyl, heterocycloalkyl, aryl, heteroaryl, and (X)—R";
wherein X is selected from the group consisting of $(CH_2)_n$, $(Ph)_n$, $O(CH_2)_n$, $NH(CH_2)_n$, $N[(CH_2)_n]_2$, and $(OCH_2CH_2)_n$;
wherein n=0 to 20;
wherein R" is selected from the group consisting of:
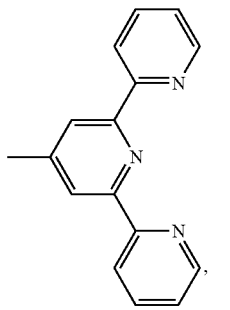
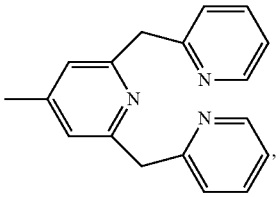
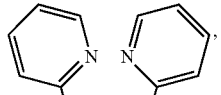
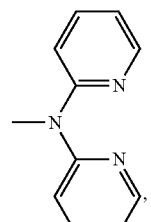
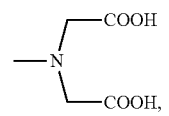
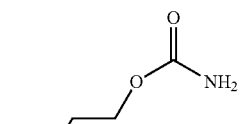
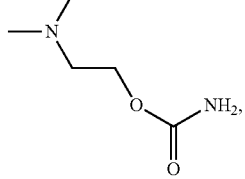
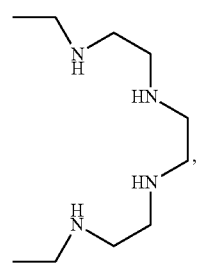

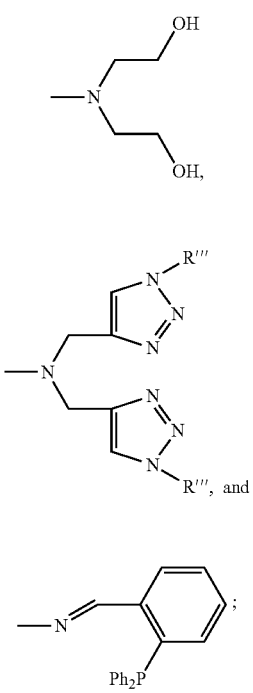

wherein R''' is selected from the group consisting of H, alkyl, unsaturated alkyl, heteroalkyl, cycloalkyl, heterocycloalkyl, aryl, heteroaryl, and (X)—R''; and wherein the backbone structure must have at least one R'' group present.

Tetraphenylethene (TPE) is an archetypal aggregation-induced emission luminogen. Through proper molecular engineering, TPEs are not only excellent emitters for the fabrication of efficient light-emitting diodes but also sensitive probes for the detection and visualization of biomolecules. To endow TPE with metal chelating ability, the TPE core was functionalized with a terpyridine moiety, due to its strong and directed metal coordination capacity. Being soluble in aqueous media, the terpyridine-containing TPEs form nanoaggregates and emit strong greenish blue light, thanks to the aggregation-induced emission characteristics of the TPE core. The emission can be gradually decreased and eventually quenched upon protonation. When exposed to different metal ions, the fluorescence of these nanoaggregates is quenched, enhanced and/or spectral-shifted. This demonstrates the terpyridine-containing TPEs' applicability as fluorescent sensors for metal ions.

Among a variety of these ions, only $Zn^{2+}$ alters the emission color to yellow effectively, demonstrating the terpyridine-containing TPEs' applicability as fluorescent zinc ion sensors. Owing to metal-to-ligand-charge-transfer, terpyridine-containing TPEs experience color change selectively in the presence of $Fe^{2+}$, which allows $Fe^{2+}$ to be distinguished from other metals with the naked eye.

In one aspect of the present subject matter, the fluorescent sensor for metal ions is selected from the group consisting of 1-[4'-(4'-2,2':6',2''-Terpyridyl)-biphenyl-4-yl]-1,2,2-triphenylethene (TPETPy) and 1,2-Bis[4'-(4'-2,2':6',2'-terpyridyl)-biphenyl-4-yl]-1,2-diphenylethene (TPE2TPy), the chemical structures of which are shown below.

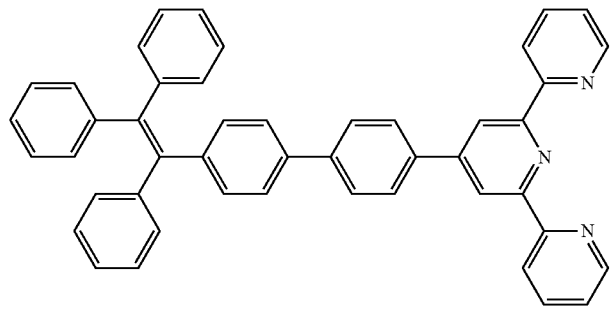

TPETPy

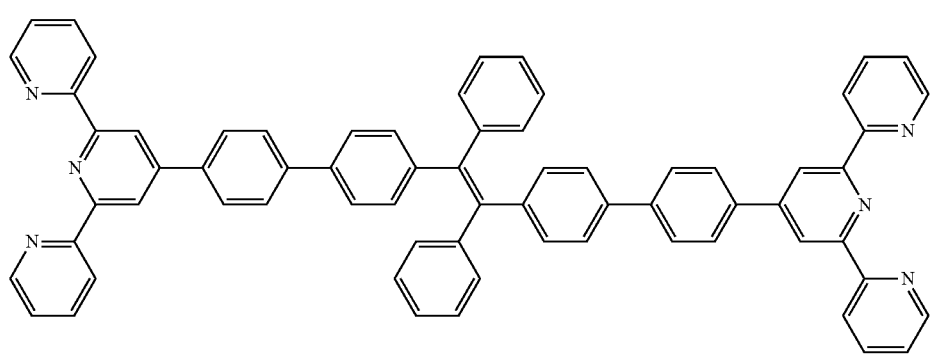

TPET2TPy

In addition, it is also an object of the present subject matter to provide a method of detecting and identifying a metal ion in a sample comprising: (a) contacting the sample with the fluorescent sensor for metal ions described above, (b) detecting fluorescence, (c) measuring the fluorescence emission intensity, and (d) identifying the metal ion based on any spectral shift signaling or intensity change of the fluorescence emission intensity.

BRIEF DESCRIPTION OF THE DRAWINGS

Various embodiments will be described in detail with reference to the accompanying drawings.

FIGS. 12A-B illustrate the determination of the stoichiometry in the binding process of TPE2TPy to $Zn^{2+}$. FIG. 14A illustrates the emission spectra of TPE2TPy/$Zn^{2+}$ complex formed by using different concentration ratios of TPE2TPy to $Zn^{2+}$ in THF. FIG. 14B illustrates the dependence of the emission peak position and PL intensity on the concentration ratio of $Zn^{2+}$ in relation to the total concentrations of TPE2TPy and $Zn^{2+}$ (10 µM), where $\lambda_{ex}$=350 nm.

FIG. 15A illustrates the fluorescence image of PMMA matrix blended with TPETPy before exposure to $Zn(ClO_4)_2$. FIG. 15B illustrates the fluorescence image of PMMA matrix blended with TPETPy after exposure to $Zn(ClO_4)_2$. FIG. 15C illustrates the fluorescence image of PMMA matrix blended with TPETPy exposed to 2,2'-dipicolylamine. FIG. 15D illustrates the fluorescence image of PMMA matrix blended with TPE2TPy before exposure to $Zn(ClO_4)_2$. FIG. 15E illustrates the fluorescence image of PMMA matrix blended with TPE2TPy exposed to $Zn(ClO_4)_2$. FIG. 15F illustrates the fluorescence image of PMMA matrix blended with TPE2TPy after exposure to 2,2'-dipicolylamine.

FIG. 16A illustrates the TPETPy-doped PMMA film covered with a shadow mask with the letter "A" exposed to the acetonitrile solution of $Zn(OCl_4)_2$. After solvent evaporation, the mask was removed before UV illumination. FIG. 16B illustrates the filter paper with the letters "HK" written thereon by an aqueous solution of $Zn(OAc)_2$. The filter paper was soaped in DCM solution of TPE2TPy followed by solvent evaporation. FIG. 16C illustrates the TLC plate soaped in TPE2TPy taken under illumination of UV light. The TLC plate was first immersed in the DCM solution of TPE2TPy. After solvent evaporation, the TLC plate was then partially dipped in aqueous solution of $Zn(OAc)_2$.

FIG. 23A illustrates the UV spectra of TPE2TPy/$Fe^{2+}$ complex formed by mixing different concentration ratios of TPE2TPy to $Fe^{2+}$ in THF/water mixtures (1:99 v/v). FIG. 23B illustrates the dependence of the absorbance at 576 nm on the concentration ratio of $Fe^{2+}$ in relation to the total concentration of TPE2TPy and $Fe^{2+}$ (10 µM).

DETAILED DESCRIPTION

Definitions

Figure 1:
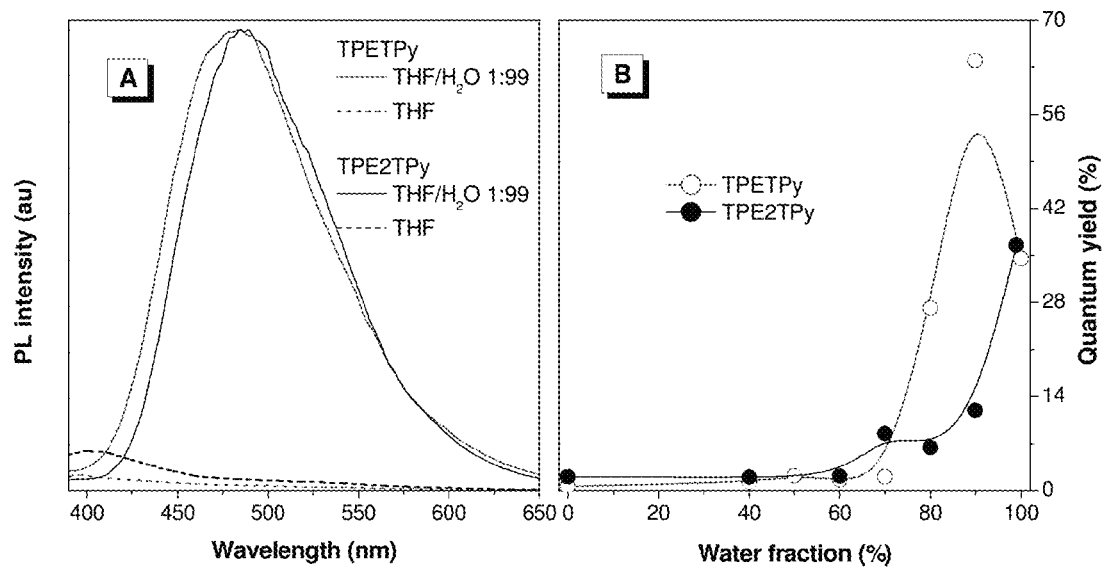
FIG. 1A illustrates the emission spectra of solutions of TPETPy and TPE2TPy in THF and THF/water mixture (1:99 v/v).
FIG. 1B illustrates the relationship between quantum yields of TPETPy and TPE2TPy and water fraction (%) of the solvent compositions of THF/water mixtures.

All technical and scientific terms used herein have the same meanings as commonly understood by someone ordinarily skilled in the art to which the present subject matter belongs. The following definitions are provided for clarity.

The phrase "aggregation caused quenching" or "ACQ" as used herein refers to the phenomenon wherein the aggregation of fluorophores significantly decreases the fluorescence intensity of the fluorophores. The aggregate formation is said to "quench" light emission of the fluorophores.

The phrase "aggregation induced emission" or "AIE" as used herein refers to the phenomenon manifested by compounds exhibiting significant enhancement of their light-emission upon aggregation in the amorphous or crystalline (solid) states whereas they exhibit weak or almost no emission in dilute solutions.

The term "alkyl" as used herein refers to a branched or unbranched hydrocarbon chain comprising a designated number of carbon atoms. For example, $C_1$-$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like. It is also contemplated as with the scope of the present subject matter that "alkyl" may also refer to a hydrocarbon chain wherein any of the carbon atoms of the alkyl are optionally replaced with O, NH, S, or $SO_2$. For example, carbon 2 of n-pentyl can be replaced with 0 to form propyloxymethyl.

The term "aryl" refers to an aromatic carbocyclic group having a single ring, for example a phenyl ring; multiple rings, for example biphenyl; or multiple condensed rings in which at least one ring is aromatic, for example naphthyl, 1,2,3,4-tetrahydronaphthyl, anthrl, or phenanthryl, which can be unsubstituted or substituted with one or more other substituents as defined above.

The term "cycloalkyl" as used herein refers to an organic cyclic substituent comprising a designated number of carbon atoms. For example, a $C_3$-$C_8$ cycloalkyl contains three to eight carbon atoms forming a three, four, five, six, seven, or eight-membered ring, including, for example, a cyclopropyl, cyclobutyl, cyclopentyl, cyclohexyl, cycloheptyl, or cyclooctyl ring, and the like.

The term "chromophore" as used herein refers to the part of a molecule responsible for its color.

The phrase "emission intensity" as used herein refers to the magnitude of fluorescence/phosphorescence normally obtained from a fluorescence spectrometer or a fluorescence microscopy measurement.

The term "fluorophore" as used herein refers to a fluorescent chemical compound that can re-emit light upon light excitation. Fluorophores typically contain several combined aromatic groups, or plane or cyclic molecules with several π bonds. Fluorophores can be used as tracers in fluids, dyes for staining certain structures, substrates of enzymes, or probes or indicators. Fluorophores absorb light energy of a specific wavelength and re-emit light at a longer wavelength. The absorbed wavelengths, energy transfer efficiency, and time before emission depend on both the fluorophore structure and its chemical environment, as the molecule in its excited state interacts with surrounding molecules.

The term "heteroaryl" as used herein refers to a heterocycle in which at least one ring is aromatic. A heterocycle is a saturated, unsaturated, or aromatic carbocyclic group having a sing ring, multiple rings, or multiple condensed rings, and having at least one hetero atom such as nitrogen, oxygen, or sulfur within at least one of the rings.

The term "luminogen" as used herein refers to an atom or atomic grouping in a chemical compound that manifests luminescence.

The term "nanoparticle" as used herein refers to any microscopic particle or particle population having a mean diameter of about 100 or less nanometers (nm); less than about 90 nm; less than about 80 nm; less than about 70 nm; less than about 60 nm; less than about 50 nm in diameter; or having a mean diameter of from 1 nm to less than 100 nm; from 10 nm to less than 100 nm; from 20 nm to less than 100 nm; from 30 nm to less than 100 nm; from 40 nm to less than 100 nm; from 50 nm to less than 100 nm; from 10 nm to 90 nm; from 20 to 80 nm; or having a mean diameter of from 30 to 70 nm. In an embodiment, greater than 99% of the nanoparticles of a nanoparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 30% of the microparticles have a mean diameter falling within a described range; greater than about 20% of the microparticles have a mean diameter falling within a described range; or greater than about 10% of the microparticles have a mean diameter falling within a described range.

The phrase "unsaturated alkyl" as used herein refers to a branched or unbranched unsaturated hydrocarbon chain comprising a designated number of carbon atoms. For example, a $C_2$-$C_6$ straight or branched alkenyl hydrocarbon chain contains 2 to 6 carbon atoms having at least one double bond, and includes but is not limited to substituents such as ethenyl, propenyl, iso-propenyl, butenyl, iso-butenyl, tert-butenyl, n-pentenyl, n-hexenyl, and the like. It is also contemplated as within the scope of the present subject matter that "unsaturated alkyl" may also refer to an unsaturated hydrocarbon chain wherein any of the carbon atoms of said unsaturated alkyl are optionally replaced with O, NH, S, or SO$_2$. For example, carbon 2 of 4-pentene can be replaced with O to form (2-propene)oxymethyl.

The term "a" or "an" as used herein includes the singular and the plural, unless specifically stated otherwise. Therefore, the term "a," "an," or "at least one" can be used interchangeably in this application.

Throughout the application, descriptions of various embodiments use the term "comprising;" however, it will be understood by one of skill in the art, that in some specific instances, an embodiment can alternatively be described using the language "consisting essentially of" or "consisting of."

For the purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

It is an object of the present subject matter to provide a fluorescent sensor for metal ions comprising a luminogen that exhibits aggregation induced emission properties functionalized with a terpyridine moiety; wherein the luminogen functionalized with terpyridine moiety comprises a backbone structure selected from the group consisting of:

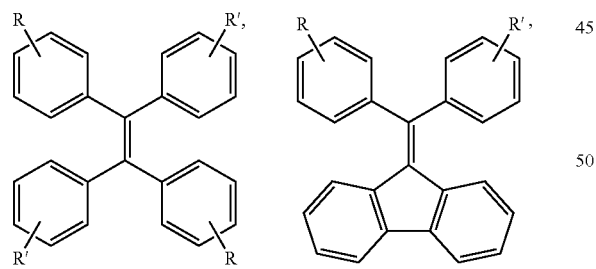

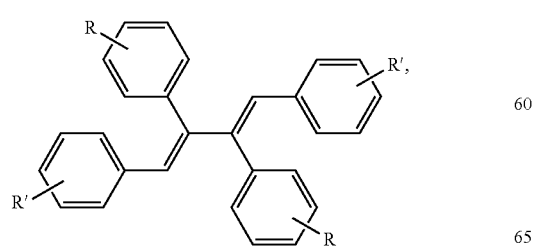

-continued

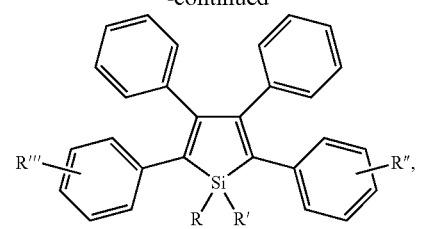

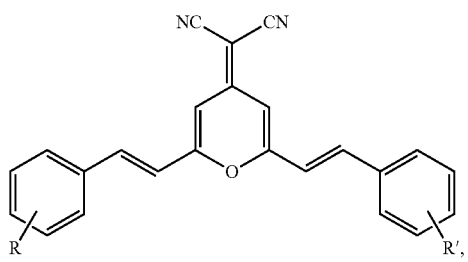

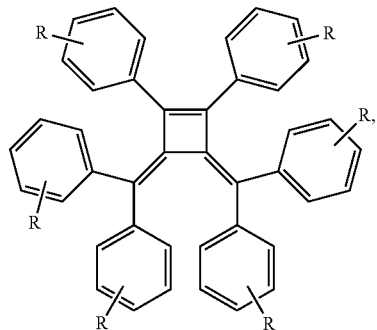

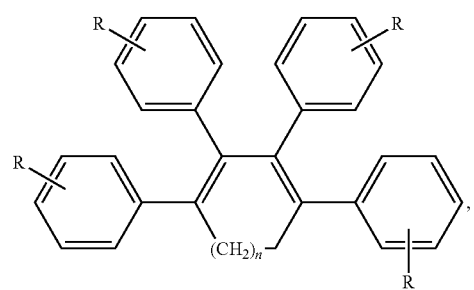

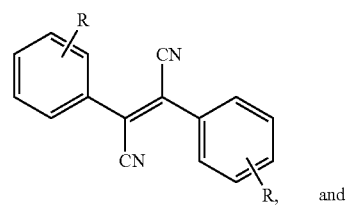

and

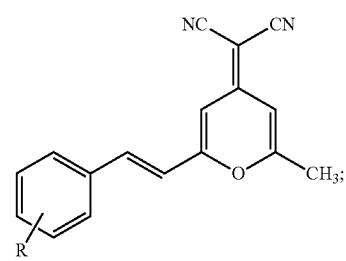

wherein R and R' are independently selected from the group consisting of H, alkyl, unsaturated alkyl, heteroalkyl, cycloalkyl, heterocycloalkyl, aryl, heteroaryl, and (X)—R";

wherein X is selected from the group consisting of $(CH_2)_n$, $(Ph)_n$, $O(CH_2)_n$, $NH(CH_2)_n$, $N[(CH_2)_n]_2$, and $(OCH_2CH_2)_n$;

wherein n=0 to 20;

wherein R" is selected from the group consisting of:

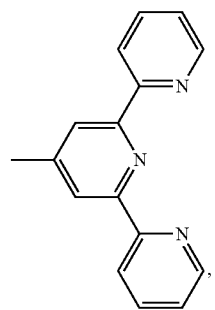

,

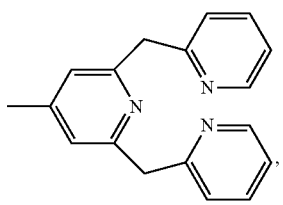

,

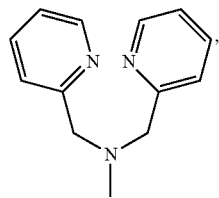

,

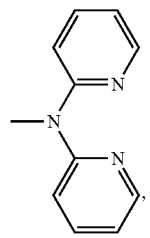

,

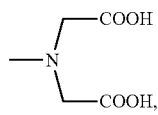

,

-continued

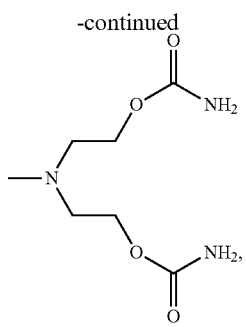

,

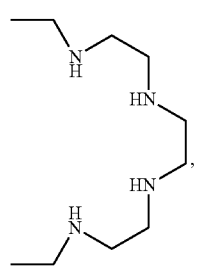

,

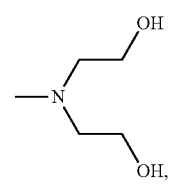

,

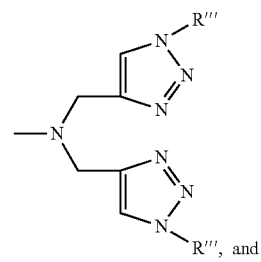

, and

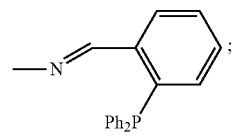

;

wherein R'" is selected from the group consisting of H, alkyl, unsaturated alkyl, heteroalkyl, cycloalkyl, heterocycloalkyl, aryl, heteroaryl, and (X)—R"; and wherein the backbone structure must have at least one R" group present.

In a further embodiment, the fluorescent sensor for metal ions described above will comprise a luminogen functionalized with terpyridine moiety selected from the group consisting of 1-[4'-(4'-2,2':6',2"-Terpyridyl)-biphenyl-4-yl]-1,2,2-triphenylethene (TPETPy) and 1,2-Bis[4'-(4'-2,2':6',2"-terpyridyl)-biphenyl-4-yl]-1,2-diphenylethene (TPE2TPy), having the chemical structures shown below.

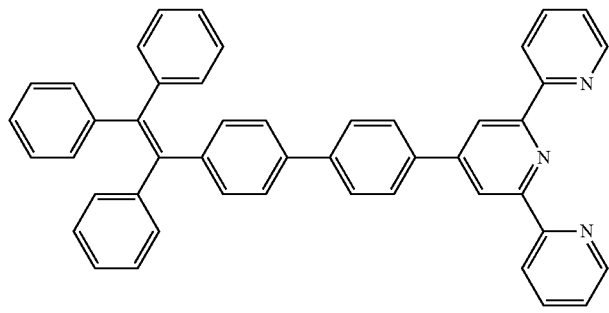

TPETPy

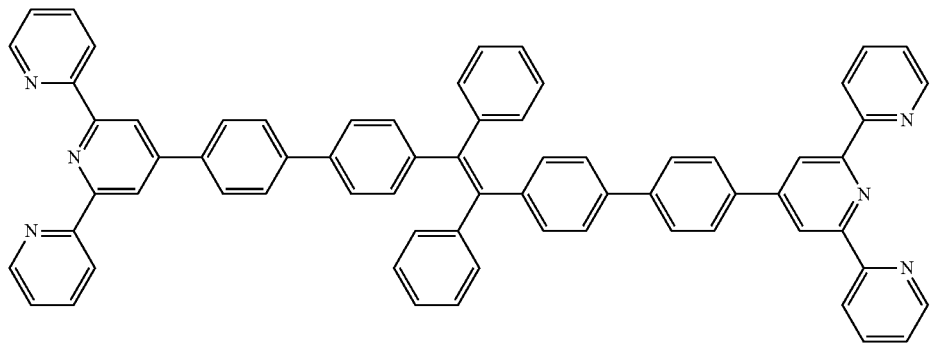

TPET2TPy

Aggregation-Induced Emission

TPETPy and TPE2TPy are practically non-luminescent when molecularly dissolved in good solvents. However, the addition of poor solvents, such as water, to solutions of TPE-TPy and TPE2TPy drastically increases the light emissions thereof. This is exemplified in FIG. 1A, which illustrates the emission spectra of solutions of TPETPy and TPE2TPy in THF and THF/water mixtures (1:99 v/v). A dilute tetrahydrofuran (THF) solution of TPETPy, for example, emits faintly at ~400 nm when photoexcited at 350 nm (FIG. 1A). However, in the THF/water mixture with 99 vol % of water, TPETPy and TPE2TPy strongly emit with peaks at about 484 nm when photoexcited at 350 nm (FIG. 1A).

Figure 2:
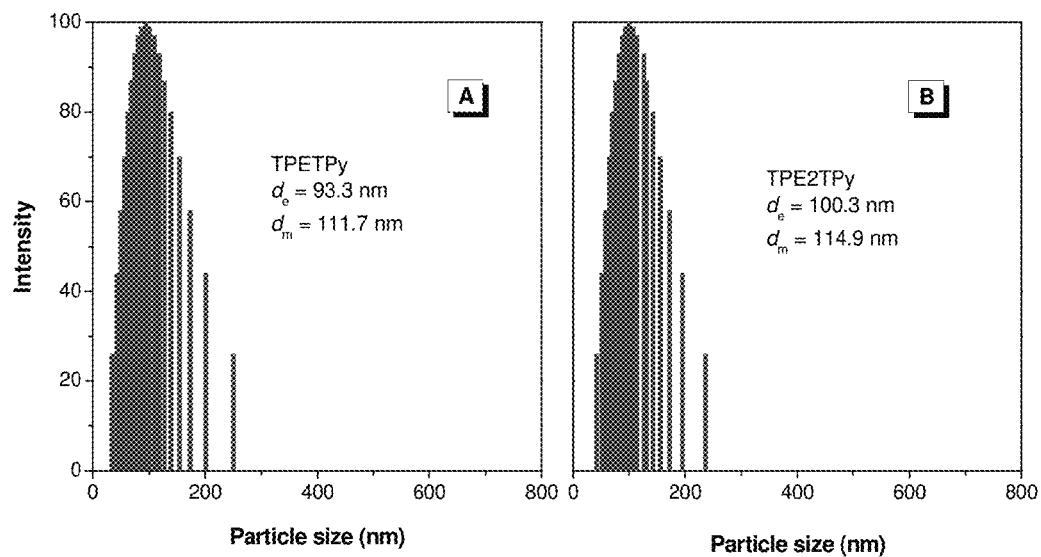
FIGS. 2A-B illustrate particle size distributions of (A) TPETPy and (B) TPE2TPy in THF/water mixture (1:99 v/v) where $d_e$ is the effective diameter and $d_m$ is the mean diameter and where TPE=2.5 µM and the metal ion=10 µM.

Since water is a poor solvent of TPETPy, TPETPy molecules aggregate in aqueous mixtures with high water fractions. Aqueous mixtures of TPETPy are transparent and homogeneous, suggesting that the dye aggregates suspended therein are nano-sized. Particle size analysis by dynamic light scattering (DLS) revealed the existence of particles with an average size of about 100 nm in solvent mixtures with 99% water (FIG. 2). This confirms that TPE molecules have indeed aggregated into nanoparticles in the mixed solvent. TPETPy is therefore induced to emit light by aggregate formation; in other words, it is aggregation-induced emission active. In the dilute THF solution, the phenyl rings of the TPE core can rotate freely against the central olefinic double bond, which nonradiatively deactivates the excited species and renders the dye non-emissive. The intramolecular motions of the nanoaggregates in the THF/water mixture (1:99 v/v) intramolecular motions are restricted, which blocks the nonradiative decay channels and makes dye molecules highly luminescent.

To have a quantitative picture, we estimated the quantum yield ($\phi_F$) values of TPEs in THF and THF/water mixtures, using quinine sulfate as standard. As shown in FIG. 1B, the $\Phi_F$ value of TPETPy in pure THF solution is merely 0.49%, which remains almost unchanged in mixed solvents with less than 60 vol % of water. Afterwards, it starts to increase swiftly. At a water fraction of 90 vol %, the $\Phi_F$ value rises to 63.9%, which is 130-fold higher than that in pure THF. The trajectory of the $\Phi_F$ change suggests that the molecularly dissolved dye molecules start to aggregate at a water fraction of ~60 vol % and the population of the aggregates increases with a further increase in the water fraction.

Similar phenomenon is observed in TPE2TPy. The $\Phi_F$ value of pure THF solution of TPE2TPy is 2.07%, which is higher than that of TPETPy. This can be explained by the aggregation-induced emission mechanism. In TPE2TPy, one more phenyl ring of the TPE core is substituted by the bulky terpyridine unit, which further blocks intramolecular rotation and hence makes TPE2TPy more emissive in the aggregate-solution state. The aggregation-induced emission effect has enabled the TPEs to emit efficiently in the solid state: the fluorescence (FL) efficiencies of the thin films ($\Phi_{F,film}$) of TPETPy and TPE2TPy determined by a calibrated integrating sphere are 74.7 and 98.7%, respectively.

The fluorescence properties of TPETPy and TPE2TPy are summarized in Table 1. Apart from the enhancement in quantum efficiency, the emission maximum ($\lambda_{em}$) of the nanoaggregates is largely red shifted as compared to their solution state. In THF solution, the phenyl rings on the TPE molecules undergo active intramolecular torsional/rotational motions against the central double bond. The TPE molecules can adopt very twisted conformations and emit at shorter wavelength. In the aggregate state, the intramolecular torsional/rotational motions are greatly suppressed. The TPE molecules assume less twisted, more stable conformations, resulting in red-shifted emission.

TABLE 1

Absorption and Emission Characteristics of TPE Derivatives in Solution (Soln)[a] and Aggregate (Aggr)[b] States

| | $\lambda_{ab}$ (nm)[c] | | $\lambda_{em}$ (nm)[d] | | |
|---|---|---|---|---|---|
| | Soln | Aggr | Soln ($\Phi_F$) | Aggr ($\Phi_F$) | Film ($\Phi_F$)[e] |
| TPETPy | 317 | 322 | 400 (0.49) | 484 (34.5) | 466 (74.7) |
| TPE2TPy | 320 | 326 | 402 (2.07) | 490 (36.5) | 475 (98.7) |

[a] In THF solution (1 μM).
[b] In THF/water (1:99 v/v) mixture (1 μM).
[c] Absorption maximum.
[d] Emission maximum with quantum yield (%) given in the parentheses; excitation wavelength: 350 nm.
[e] Solid state quantum yield determined by a calibrated integrating sphere.

On the other hand, thin films of the TPE molecules emit at shorter wavelengths than their aggregates in solution. This may be due to the degree of aggregation as well as the packing mode. In a solid thin film, a poly(methyl methacrylate) (PMMA) matrix can serve as a solid "solvent" to disperse the TPE molecules. The emission comes from sole TPE molecules with their intramolecular motions restricted in the solid matrix. In one instance, the TPE derivatives can take on relatively twisted but rigid structures and thus emit more intensely at shorter wavelength. In THF/water mixture with high water fraction, the molecules can abruptly agglomerate into amorphous aggregates with solvent trapped inside. Inside these "loose" particles, the TPE molecules may still undergo partial intramolecular motions, which make them less emissive than in solid film. Without the solid constraint, the TPE molecules in the amorphous phase can assume a more planar conformation and thus exhibit luminescence at longer wavelength.

pH Effect on Emission

Figure 3:
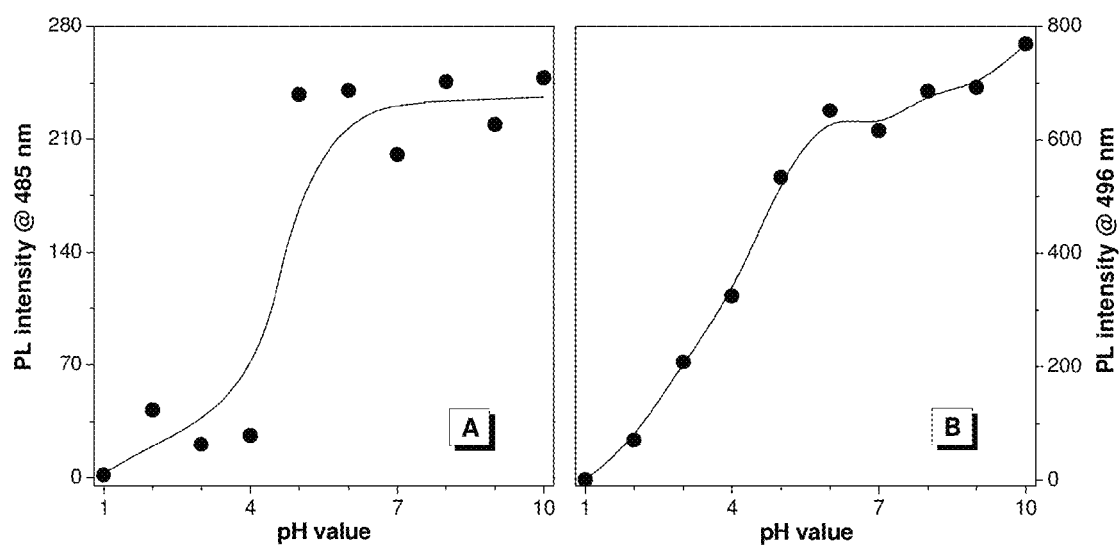
FIGS. 3A-B illustrate the change in FL intensity of (A) TPETPy and (B) TPE2TPy in aqueous buffer with different pH values, where TPE=1.0 µM and $\lambda_{ex}$=350 nm.

Terpyridine has acidic and basic functionalities. Therefore, the luminescence of terpyridine-containing TPEs can be affected by changes in pH. In neutral and basic aqueous solution (pH>7), molecules of TPETPy and TPE2TPy aggregate and emit (FIG. 3). The emission, however, is weakened in a low pH medium. At a low pH, the pyridine units can be protonated and transformed into pyridium salts, which may make the TPE molecules soluble in water. Due to the aggregation-induced emission properties of TPE, the genuine dissolution of TPE at the molecular level in an acidic medium turns off the emission thereof.

Figure 4:
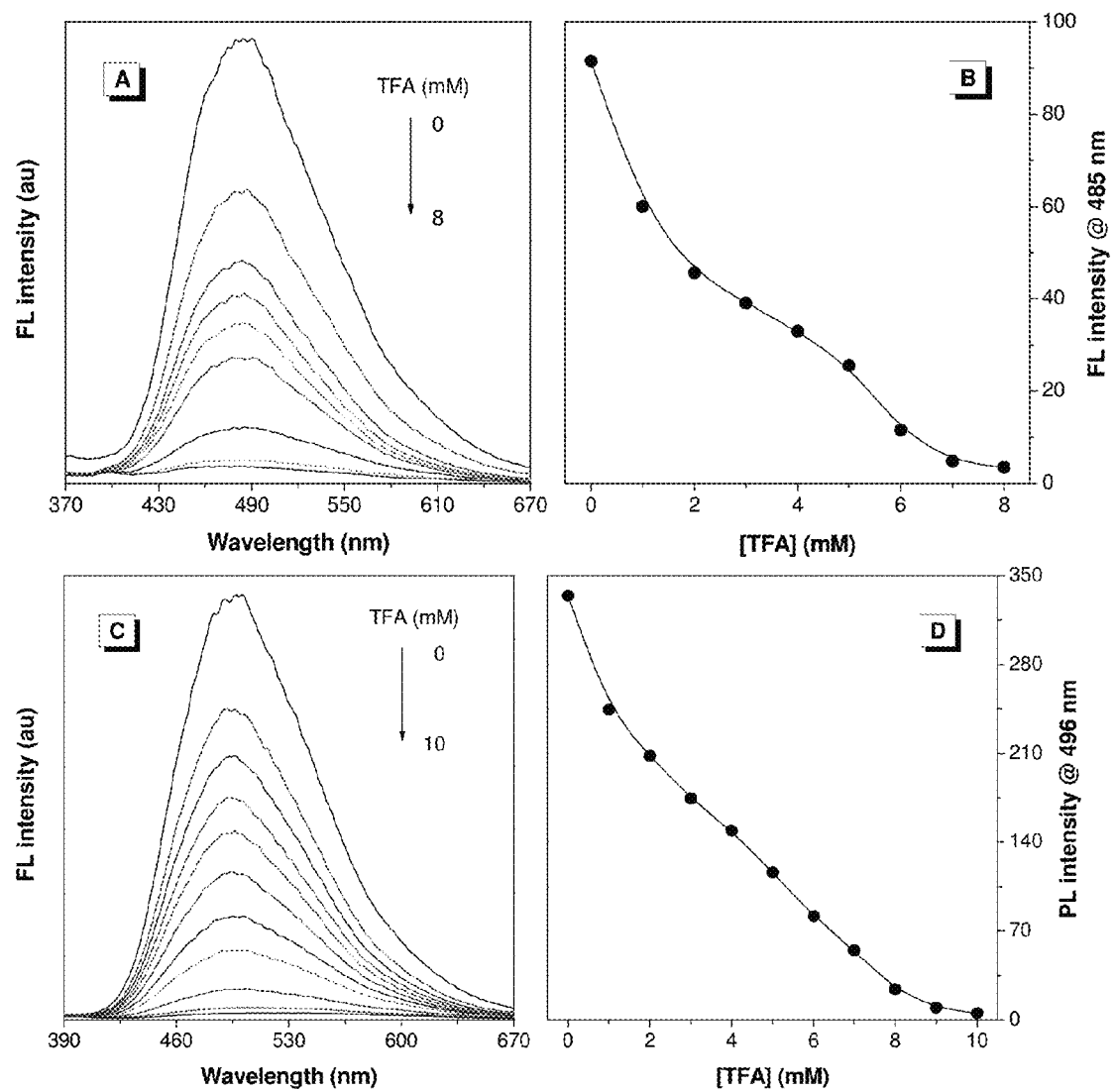
FIG. 4A illustrates the emission spectra of TPETPy in THF/water mixtures (1:99 v/v) with different amounts of trifluoroacetic acid (TFA), where TPE=µM and $\lambda_{ex}$=350 nm.
FIG. 4B illustrates the change in FL intensity of TPETPy with TFA concentration, where TPE=µM and $\lambda_{ex}$=350 nm.
FIG. 4C illustrates the emission spectra of TPE2TPy in THF/water mixtures (1:99 v/v) with different amounts of TFA, where TPE=µM and $\lambda_{ex}$=350 nm.
FIG. 4D illustrates the change in FL intensity of TPE2TPy with TFA concentration, where TPE=µM and $\lambda_{ex}$=350 nm.

As shown in FIG. 4A, the addition of trifluoroacetic acid (TFA) to TPE solutions in THF/water mixtures decreases the fluorescence thereof. The aqueous solution of TPETPy without any added TFA emits an intense greenish-blue light at 485 nm. However, the addition of 1 mM of TFA into the solution decreases the emission by ~30%. Further addition of TFA gradually weakens and eventually quenches the emission. Upon addition of TFA, the terpyridine units of TPETPy are ionized, which makes the dye molecules more or less soluble in water and hence the light emission is quenched. With the increase in TFA concentration, more TPETPy molecules are protonated and therefore TPETPy has weaker emissions (FIG. 4B).

Figure 5:
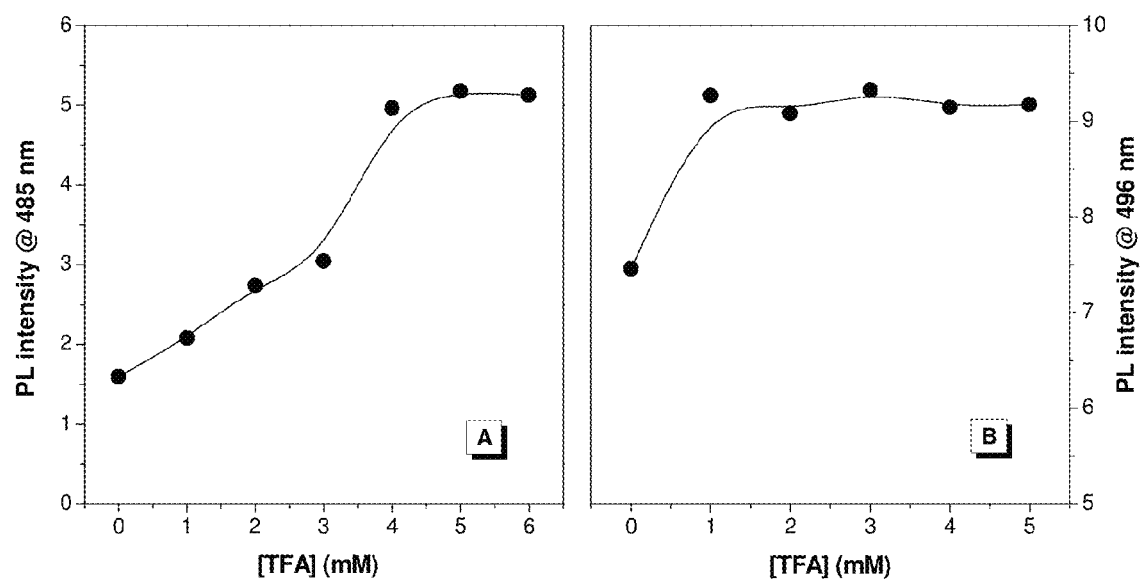
FIGS. 5A-B illustrates the change in FL intensity of (A) TPETPy and (B) TPE2TPy with different amounts of TFA concentration in THF, where TPE=µM and $\lambda_{ex}$=350 nm.

In contrast, the emission of the THF solution of TPETPy is enhanced upon addition of TFA (FIG. 5A). THF is a good solvent for TPETPy. Therefore, TPETPy is weakly fluorescent in THF due to the aggregation-induced emission mechanism. Accordingly, in the presence of TFA, TPETPy in THF is protonated and becomes less soluble in THF. In this instance, the TPETPy molecules start to aggregate and therefore fluoresce. The same phenomenon is observed with TPE2TPy (FIGS. 4C, 4D, and 5B).

Metal Ion Sensor

Since terpyridine is a well-known metal chelating unit, TPETPy and TPE2TPy can be utilized as chemosensors for metal ions. In one embodiment, the fluorescent sensors for metal ions can be used to detect and identify metal ions selected from the group consisting of zinc, iron, copper, cadmium, and mercury ions.

Figure 6:
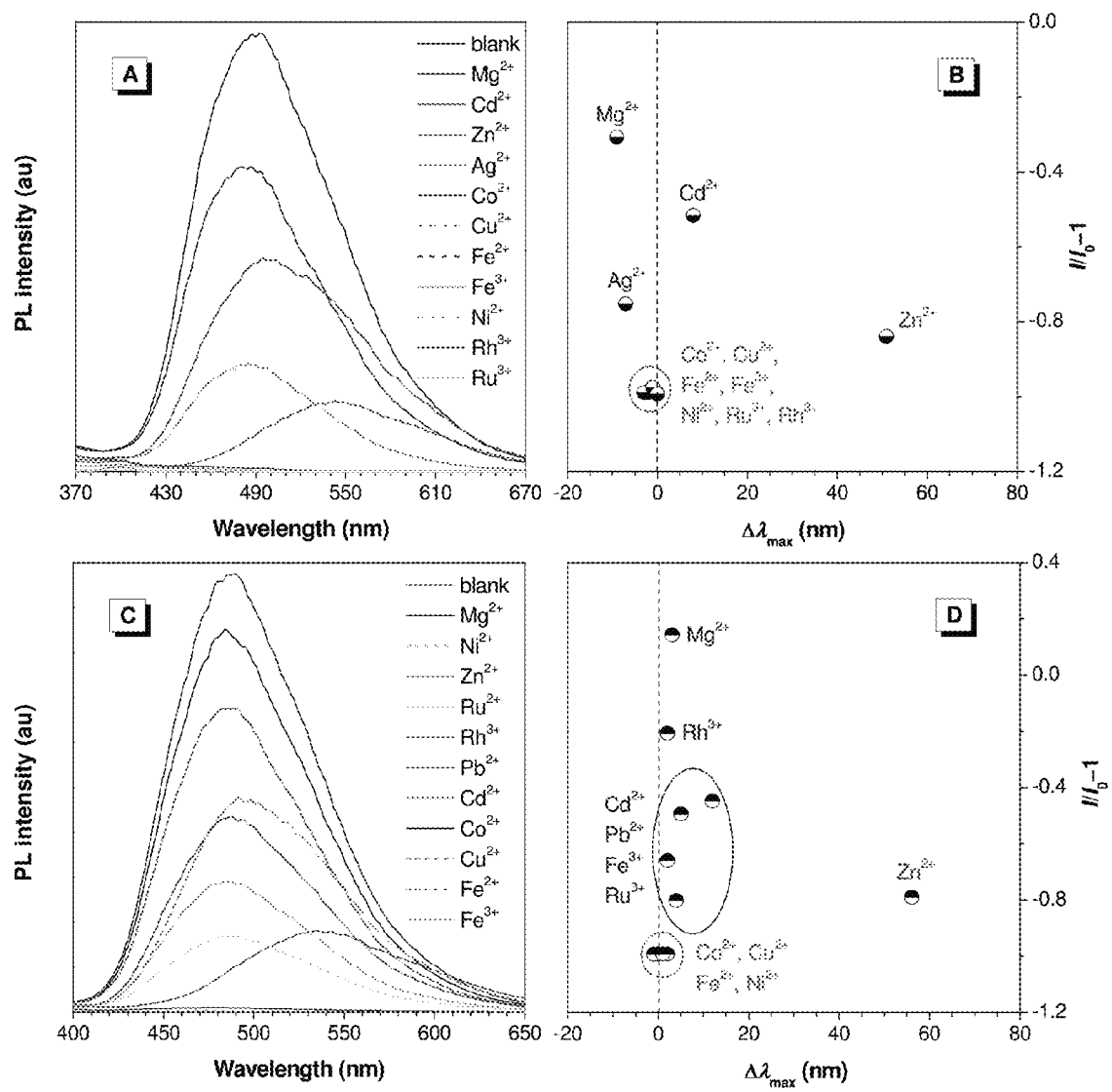
FIG. 6A illustrates the emission spectra of TPETPy in the presence of various cations in THF/water mixtures (1:99 v/v).
FIG. 6B illustrates the FL response of nanoaggregates of TPETPy to cations. The x-axis and y-axis correspond to the shift in the emission maximum ($\lambda_{max}$) and the enhancement of FL intensity with respect to the FL spectra without metal ions, respectively.
FIG. 6C illustrates the emission spectra of TPETPy in the presence of various cations in THF/water mixtures (1:99 v/v).
FIG. 6D illustrates the FL response of nanoaggregates of TPE2TPy to cations. The x-axis and y-axis correspond to the shift in the emission maximum ($\lambda_{max}$) and the enhancement of FL intensity with respect to the FL spectra without metal ions, respectively.

FIG. 6A shows the fluorescence response of the nanoaggregates of TPETPy to various metal ions. Since terpyridine does not coordinate with alkali metal cations, $Na^+$ and $K^+$ exert no effect on the fluorescence of TPETPy. The spectral pattern, shown in FIG. 6A, continues to be unchanged in the presence of $Mg^{2+}$ and $Ag^{2+}$ ions but the fluorescence becomes weaker. When exposed to $Cd^{2+}$ and $Zn^{2+}$, the FL spectra show a significant bathochromic shift. $Cu^{2+}$ and group VIIIA metal ions ($Fe^{2+}$, $Fe^{3+}$, $Co^{2+}$, $Ni^{2+}$, $Ru^{3+}$, $Rh^{3+}$, etc.) efficiently quench the emission of TPETPy.

The emission spectra of TPE2TPy upon exposure to different cations are shown in FIG. 6C. In the presence of $Mg^{2+}$ the emission of the nanoaggregates of TPE2TPy is enhanced, instead of quenched, by 10%. Its fluorescence is weakened upon exposure to $Fe^{3+}$, $Ru^{3+}$, $Rh^{3+}$, and $Pb^{2+}$, and completely quenched by $Fe^{2+}$, $Co^{2+}$, $Ni^{2+}$, and $Cu^{2+}$. Similar to TPETPy, the emission spectra shift to the redder region when $Cd^{2+}$ and $Zn^{2+}$ ions are added.

Therefore, another object of the present subject matter is provide a method of detecting and identifying a metal ion in a sample comprising: (a) contacting the sample with the fluorescence sensor for metal ions, (b) detecting fluorescence, (c) measuring the fluorescence emission intensity, and (d) identifying the metal ion based on any spectral shift signaling or intensity change of the fluorescence emission intensity.

Fluorogenic Zn(II) Sensor

Figure 7:
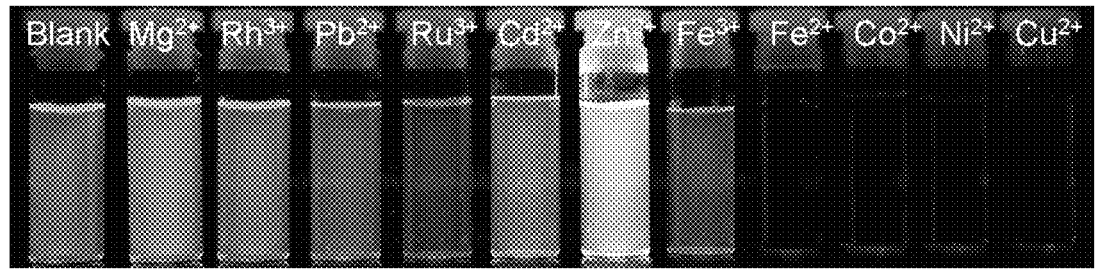
FIG. 7 is a photograph of the aqueous solutions of TPE2TPy/cation mixtures taken under UV illumination.

In a preferred embodiment, the fluorescent sensors for metal ions can be used to detect and identify zinc ions. The change in the FL intensity and the emission maximum ($\lambda_{max}$) of TPEs with various metal ions are summarized in FIGS. 6B and D. The $\lambda_{max}$ values of both TPETPy and TPE2TPy are red shifted by about 50 nm to 540 nm in the presence of $Zn^{2+}$. However, $Cd^{2+}$ ions only exert a 10 nm bathochromic shift under the same experimental conditions. Generally, it is difficult for most fluorophores to discriminate $Cd^{2+}$ and $Zn^{2+}$ because they are in the same group of the Periodic Table and exhibit similar properties. The fluorophores presented here show green emission in the presence of $Cd^{2+}$ but yellow emission when reacted with $Zn^{2+}$, thus allowing differentiation between the two cations (FIG. 7).

Figure 8:
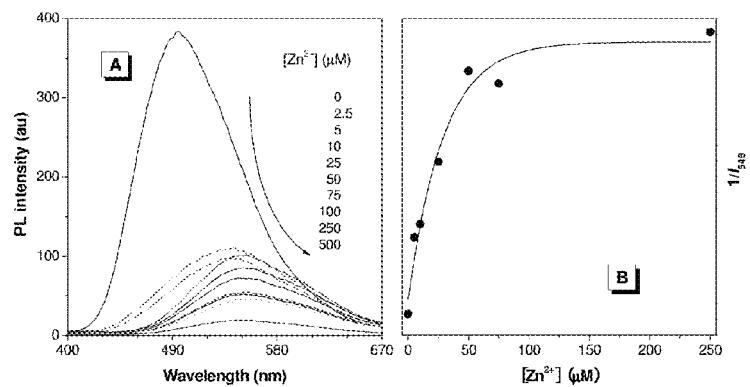
FIG. 8A illustrates the emission spectra of TPE2TPy in the presence of different concentrations of $Zn^{2+}$ in THF/water mixture (1:99 v/v) where TPE=1.0 µM and $\lambda_{ex}$=350 nm.
FIG. 8B illustrates the reciprocal of FL intensity at 545 nm in relation to the concentration of $Zn^{2+}$ where TPE=1.0 µM and $\lambda_{ex}$=350 nm.
Figure 9:
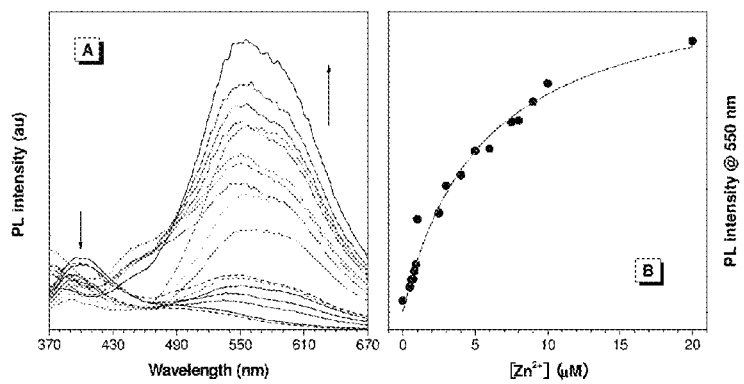
FIG. 9A illustrates the emission spectra of TPE2TPy in the presence of different concentrations of $Zn^{2+}$ in THF, where TPE=2.5 µM and $\lambda_{ex}$=350 nm.
FIG. 9B illustrates the FL intensity of TPE2TPy recorded at 550 nm in relation to the concentration of $Zn^{2+}$, where TPE=2.5 µM and $\lambda_{ex}$=350 nm.

The emission spectra of TPE2TPy upon titration with $Zn^{2+}$ are shown in FIG. 8A. In aqueous solution, the hydrophobic TPE2TPy molecules form nanoaggregates, which emit strongly at 490 nm. Addition of $Zn^{2+}$ ions into the solution gradually red-shifts the spectrum and decreases the emission. Change of the FL intensity with respect to the $Zn^{2+}$ concentration is shown in FIG. 8B, which facilitates quantitative analysis of $Zn^{2+}$ in aqueous media. TPE2TPy is non-emissive in THF. Addition of $Zn^{2+}$ [e.g., $Zn(ClO_4)_2$] into the THF solution, however, turns on the emission and generates a pronounced emission peak at about 550 nm (FIG. 9).

The binding stoichiometry for TPE2TPy and $Zn^{2+}$ was determined by the continuous variation method of analysis. The concentrations of TPE2TPy and $Zn^{2+}$ were varied, while the sum of the two concentrations was kept constant at 10.0 µM. As can be seen from FIG. 10A, with an increase in the $Zn^{2+}$ concentration, there is a decrease in emission intensity accompanied by a spectral shift to a longer wavelength region. The change in the $\lambda_{max}$ with respect to the concentration ratio of $Zn^{2+}$ to TPE2TPy is shown in FIG. 10B. At equal molar concentration, the $\lambda_{max}$ value is the largest and equal to 540 nm. Further incremental increases of $Zn^{2+}$ concentration do not change the peak position; it stays at 540 nm. The corresponding binding ratio is thus given as 1:1 for TPE2TPy to $Zn^{2+}$, which is consistent with the reported binding mode of terpyridine to $Zn^{2+}$.

Figure 11:
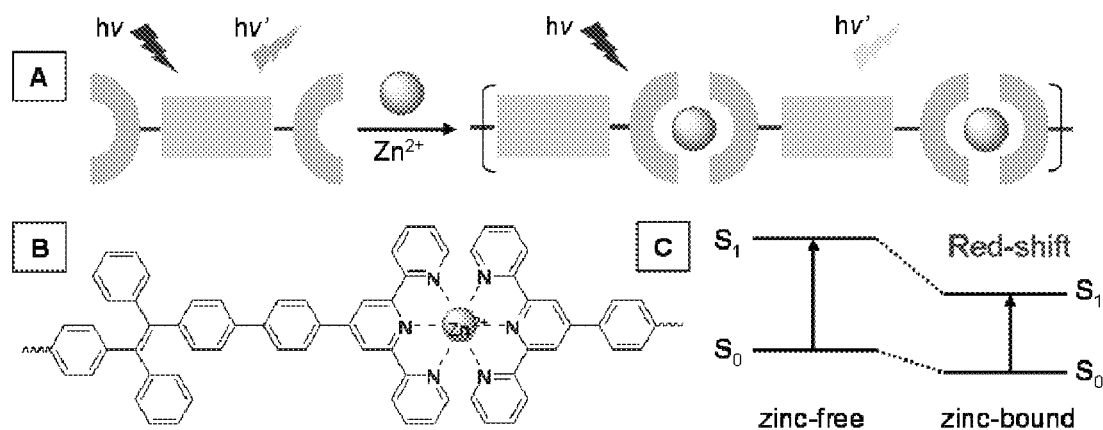
FIG. 11 illustrates (A) the possible stoichiometry of zinc-TPE2TPy complex, (B) the structure of zinc-bound TPE2TPy, and (C) the proposed mechanism for the spectral red-shift of TPE2TPy upon binding to $Zn^{2+}$.
Figure 12:
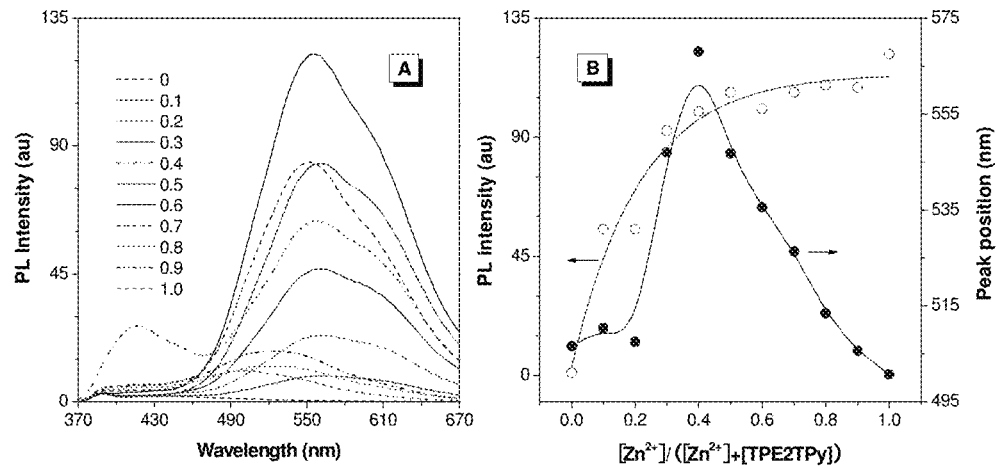
FIG. 12A illustrates the emission spectra of TPE2TPy/$Zn^{2+}$ complex formed by using different concentration ratios of TPE2TPy to $Zn^{2+}$ in THF/water mixtures (1:99 v/v).
FIG. 12B illustrates the dependence of the emission peak position on the concentration ratio of $Zn^{2+}$ in relation to the total concentrations of TPE2TPy and $Zn^{2+}$ (10 µM), where $\lambda_{ex}$=350 nm.

FIG. 11A illustrates the formation of the $Zn^{2+}$-TPE2TPy complex according to the 1:1 binding ratio, in which two terpyridine units from adjacent TPE2TPy molecules coordinate with a zinc ion to form oligomeric or polymeric complex. A similar binding mode of TPE2TPy to $Zn^{2+}$ is deduced in THF solution, indicating the aggregation of the dye molecules would not affect the coordination of the substituted ligands with $Zn^{2+}$ (FIG. 12).

Figure 13:
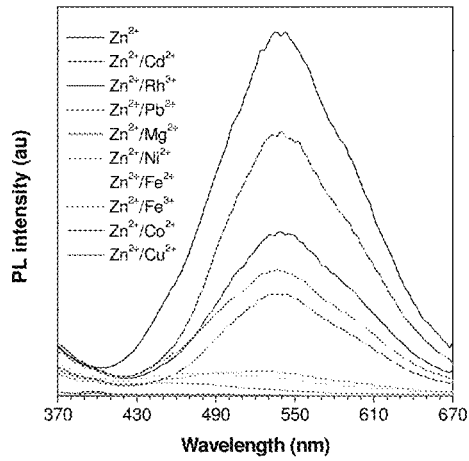
FIG. 13 illustrates the emission spectra of THF/water mixtures (1:99 v/v) of TPE2TPy/$Zn^{2+}$ complex containing various metal ions, where TPE=2.5 µM, $Zn^{2+}$=10 µM, metal ion=10 µM, and $\lambda_{ex}$=350 nm.

The selective binding ability of TPE2TPy for $Zn^{2+}$ over other metal ions was investigated by measuring the FL of TPE2TPy with $Zn^{2+}$ ions in the presence of other competitive cations. As shown in FIG. 13, the characteristic emission of the TPE2TPy/$Zn^{2+}$ complex is still observed at about 540 nm when $Cd^{2+}$, $Rh^{3+}$, $Pb^{2+}$, and $Mg^{2+}$ are added albeit in a lower intensity, implying that these metal ions interfere little with the affinity of TPE2TPy to $Zn^{2+}$. The emission is quenched by $Fe^{2+}$, $Fe^{3+}$, $Co^{2+}$, $Ni^{2+}$, and $Cu^{2+}$ due to the strong electron transfer between TPE2TPy and these metal cations. The bathochromic shift of TPE2TPy upon interaction with $Zn^{2+}$ can be ascribed to intramolecular charge transfer (ICT) effect.

Figure 14:
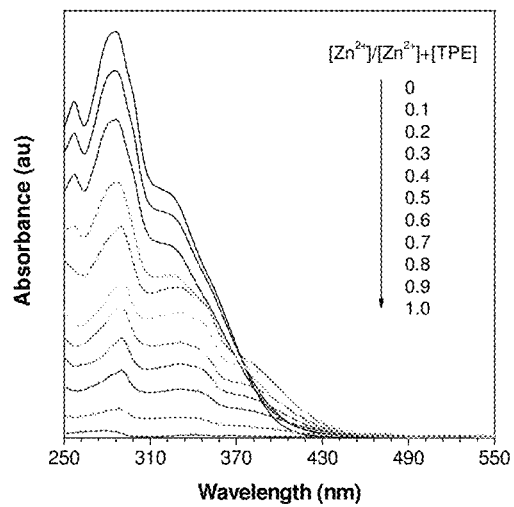
FIG. 14 illustrates the UV spectra of TPE2TPy/$Zn^{2+}$ complex formed by mixing different concentration ratios of TPE2TPy in relation to $Zn^{2+}$ in THF/water mixture (1:99 v/v). The total concentration of TPE2TPy and $Zn^{2+}$ is kept at 10 µM.

Terpyridine is slightly electron-withdrawing as compared to the TPE core. The electron withdrawing character of terpyridine is intensified upon the formation with $Zn^{2+}$, which promotes the occurrence of the ICT process from TPE core to the terpyridine-$Zn^{2+}$ moiety. The push-pull effect is strengthened and therefore can shift the emission to the longer wavelengths. Alternatively, the band gap can become narrower when the terpyridine-$Zn^{2+}$ complex forms. As shown in FIG. 14, a new peak in absorption spectra appears upon formation with $Zn^{2+}$. Due to the electron-withdrawing nature of the terpyridine ligand, the energy level of the lowest unoccupied molecular orbital will decrease more significantly than the highest occupied molecular orbital upon formation with metal, thus leading to the red shift of the spectrum (FIG. 11C).

Figure 15:
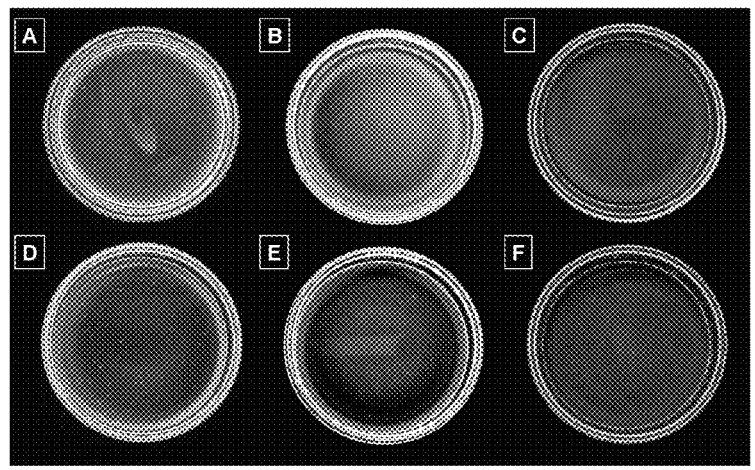
FIGS. 15A-F illustrate the fluorescence images of PMMA matrices blended with TPETPy and TPE2TPy before and after exposure to $Zn(ClO_4)_2$ and the fluorescence images of PMMA matrices blended with TPETPy and TPE2TPy exposed to 2,2'-dipicolylamine.
Figure 16:
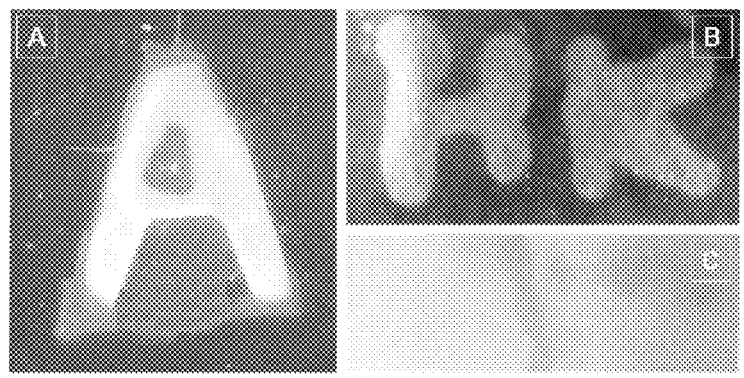
FIGS. 16A-C illustrate the $Zn^{2+}$-induced fluorescence change shown in different matrices.

As shown in FIG. 15, PMMA films doped with TPETPy and TPE2TPy were fabricated to produce highly fluorescent plastic materials for metal sensing. Exposure of the films to a solution of $Zn^{2+}$ ions caused the change of emission color from blue to green or yellow (FIG. 15). The blue emission of the thin films can be recovered by treatment with a zinc competitor, such as 2,2'-dipicolylamine. Due to the aggregation-induced emission feature, the sensing of $Zn^{2+}$ ions by terpyridine-substituted TPEs can be applicable in different solid substrates, such as filter paper and thin layer chromatography (TLC) plate (FIG. 16).

Accordingly, it is an object of the present subject matter to provide a fluorescence sensor for metal ions, wherein the luminogen functionalized with terpyridine moiety forms a complex with a metal ion which intensifies the fluorescence of the fluorescence sensor. The metal ion can be selected from the group consisting of zinc, iron, copper, cadmium, and mercury ions, with zinc ions being preferred.

In a further embodiment, the present subject matter is related to a method for detecting and identifying a metal ion in a sample comprising: (a) contacting the sample with the fluorescence sensor for metal ions wherein the luminogen functionalized with terpyridine moiety forms a complex with a metal ion, thereby intensifying the fluorescence of the fluorescence sensor, (b) detected fluorescence, (c) measuring the fluorescence emission intensity, and (d) identifying the metal ion based on any spectral shift signalling or intensity change of the fluorescence emission intensity.

In a further embodiment, the method can be used to detect and identify metal ions selected from the group consisting of zinc, iron, copper, cadmium, and mercury, with zinc ions being preferred.

Chromogenic Fe(II) Sensor

Figure 17:
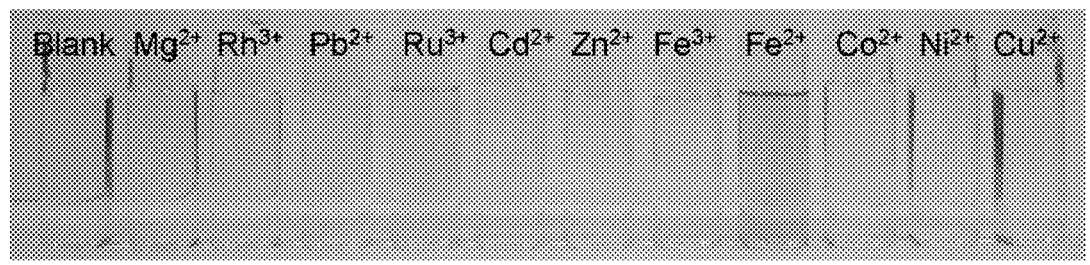
FIG. 17 is a photograph of the aqueous solutions of TPE2TPy/cation mixtures taken under daylight.
Figure 18:
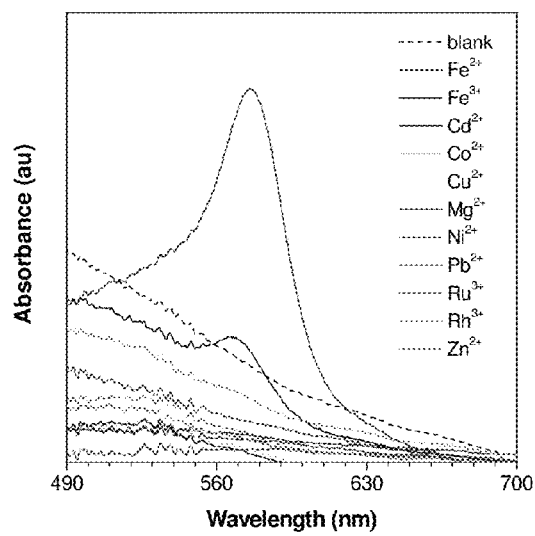
FIG. 18 illustrates the UV spectra of THF/water mixtures (1:99 v/v) of TPE2TPy containing various cations, where TPE=2.5 µM, and the metal ion=10 µM.

The nanoaggregates of TPE2TPy are capable of distinguishing $Fe^{2+}$ from $Fe^{3+}$. The fluorescence of TPE2TPy decreases slightly when in contact with $Fe^{3+}$ but is quenched by $Fe^{2+}$ at the same concentration (FIG. 7). Meanwhile, the color of the solution changes from pale yellow to light magenta in the presence of $Fe^{2+}$ but remains unchanged when admixed with $Fe^{3+}$ (FIG. 17). The selective response of TPE2TPy toward $Fe^{2+}$ and $Fe^{3+}$ are shown in FIG. 18. An absorption peak at 576 nm stands out in the presence of $Fe^{2+}$, which is responsible for the solution color change. Terpyridine-containing chemosensors are reported to respond to both $Fe^{2+}$ and $Fe^{3+}$. The color change, however, is only observed in TPE2TPy upon exposure to $Fe^{2+}$ but not $Fe^{3+}$, making TPE2TPy useful for the differentiation of iron species in different oxidative states.

Figure 19:
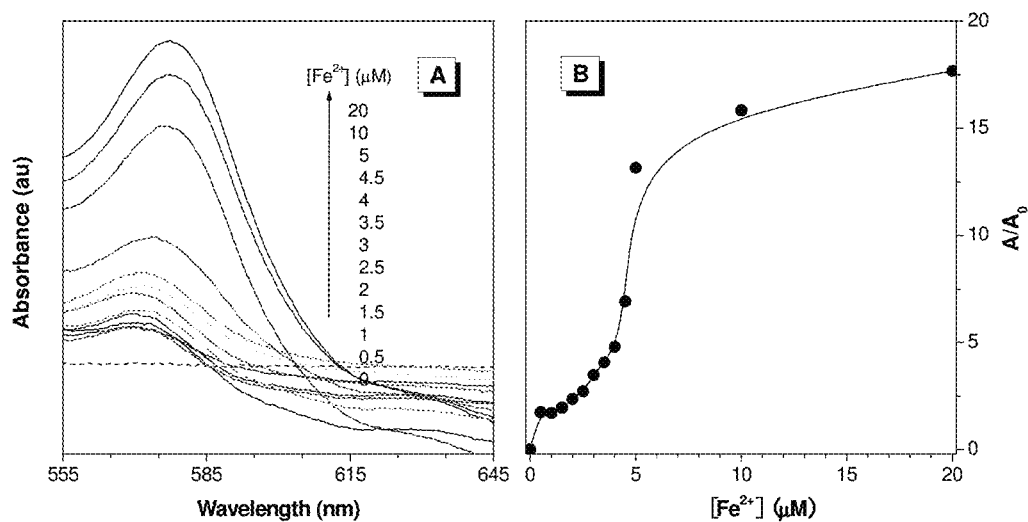
FIG. 19A illustrates the UV spectra of TPE2TPy in the presence of ferrous ions in THF/water mixtures (1:99 v/v), where TPE=2.5 µM.
FIG. 19B illustrates the relative absorbance response recorded at 575 nm, where TPE=2.5 µM.
Figure 20:
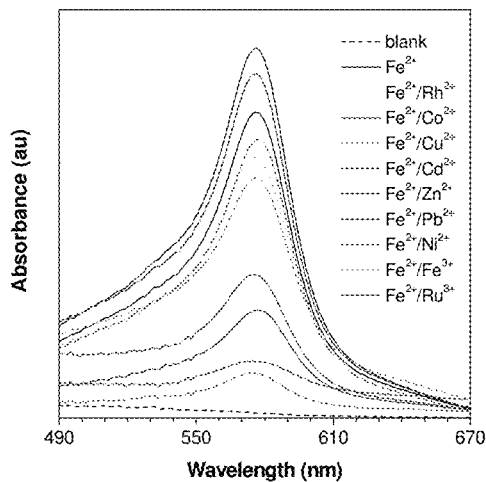
FIG. 20 illustrates the UV spectra of TPE2TPy/$Fe^{2+}$ complex in THF/water mixtures (1:99 v/v) containing different metal ions, where TPE2TPy=5 µM, metal ion=10 µM, and $Fe^{2+}$=10 µM.

The UV spectra of TPE2TPy upon titration of $Fe^{2+}$ are shown in FIG. 19. The characteristic absorption peak at 576 nm appears even in the presence of low concentration of $Fe^{2+}$. The absorbance at this wavelength continues to increase with the increase of $Fe^{2+}$ concentration. The band at 576 nm corresponds to the metal-to-ligand-charge-transfer. To determine the selectivity of TPE2TPy toward $Fe^{2+}$, cross-contamination assays were performed. As shown in FIG. 20, although the absorbance varies in the presence of other metal species, the peak at 576 nm can still be discernable with ease, indicating the high selectivity of TPE2TPy toward $Fe^{2+}$.

Figure 10:
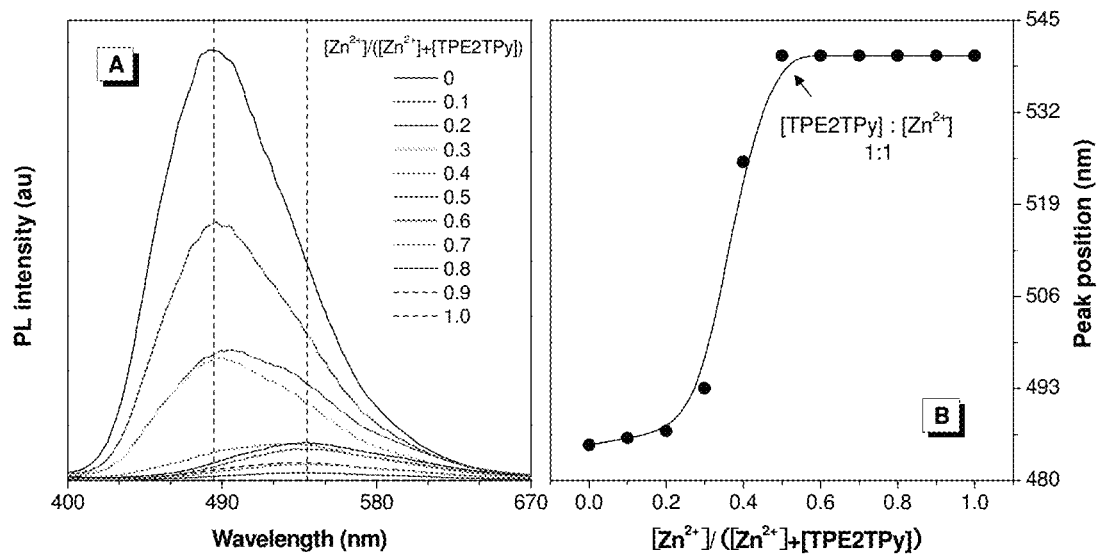
FIGS. 10A-B illustrate the determination of the stoichiometry in the binding process of TPE2TPy to $Zn^{2+}$.
Figure 21:
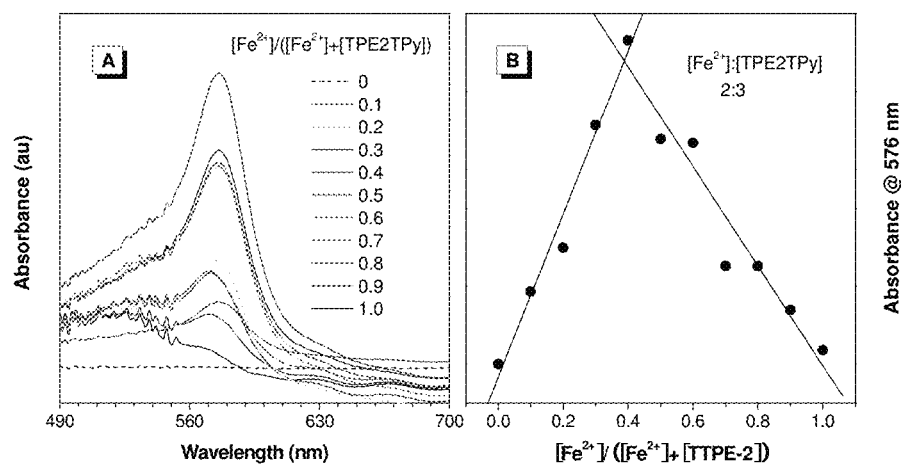
FIGS. 21A-B illustrate the determination of the stoichiometry in the binding process of TPE2TPy to $Fe^{2+}$.

The binding ratio of TPE2TPy to $Fe^{2+}$ is estimated by using continuous variation method. Since only TPE2TPy/$Fe^{2+}$ gives the characteristic absorption band at 576 nm, the absorbance at this wavelength can be considered to be proportional to the population of organic-inorganic hybrid (FIG. 21A). The Job plot shown in FIG. 21B indicates that the complex is formed in an approximately 2:3 ratio. To determine whether the nanoaggregates are dissociated or not after coordination with metal ions, particle size analyses by DLS were performed. The results are illustrated in Table 2, below. Interestingly, the changes of the particle size agree with the results from the continuous variation method. With $Zn^{2+}$, the size of the particles expands from about 100 to 400 nm, implying the formation of oligomeric/polymeric species (FIG. 10). The particle size of TPE2TPy nanoaggregates increases slightly when coordinated with $Fe^{2+}$ ions, suggesting that the aggregates are not dissociated after coordination with metal ions.

TABLE 2

Particle Size Analysis of Dye Aggregates by Dynamic Light Scattering

| | $d_e$ (nm)[a] | $d_m$ (nm)[b] | PD[c] |
|---|---|---|---|
| TPETPy | 93.3 | 111.7 | 0.432 |
| TPETPy/$Zn^{2+}$ | 294.8 | 362.0 | 0.508 |

TABLE 2-continued

Particle Size Analysis of Dye Aggregates
by Dynamic Light Scattering

| | $d_e$ (nm)[a] | $d_m$ (nm)[b] | PD[c] |
|---|---|---|---|
| TPETPy/Fe$^{2+}$ | 466.8 | 532.4 | 0.301 |
| TPE2TPy | 100.3 | 114.9 | 0.313 |
| TPE2TPy/Zn$^{2+}$ | 382.7 | 422.6 | 0.220 |
| TPE2TPy/Fe$^{2+}$ | 150.0 | 170.1 | 0.285 |

[a]Effective diameter.
[b]Mean diameter.
[c]Polydispersity.

In summary, while terpyridine-containing TPE derivatives are practically non-luminescent in the solution state, their nanoaggregates in aqueous media or films are highly emissive, demonstrating a novel phenomenon of aggregation-induced emission. The emission of the nanoaggregates of these TPEs is pH-driven and is quenched by protonation of their terpyridine units. The TPEs can function as "turn-off" fluorescent chemosensors for metal ions. Furthermore, addition of Zn$^{2+}$ ions changes the solution color from greenish blue to yellow and shifts the emission spectra by 50 nm, allowing the determination of Zn$^{2+}$ ions from other metal cations. The TPEs can also work as highly selective colorimetric sensors for Fe$^{2+}$, as demonstrated by the obvious color change of their aqueous solutions from colorless to light magenta in the presence of Fe$^{2+}$.

EXAMPLES

The examples below demonstrate various embodiments of the present subject matter.

Terpyridine-containing TPEs 1-[4'-(4'-2,2':6',2"-terpyridyl)-biphenyl-4-yl]-1,2,2-triphenylethene (TPETPy) and 1,2-bis[4'-(4'-2,2':6',2"-terpyridyl)-biphenyl-4-yl]-1,2-diphenylethene (TPE2TPy) were prepared according to the synthetic routes shown in the reaction schemes below. 4'-(4-Bromophenyl)-2,2':6',2"-terpyridine was synthesized under a benign reaction condition using poly(ethylene glycol) as medium. Suzuki coupling of 4'-(4-bromophenyl)-2,2':6',2"-terpyridine with 4-(1,2,2-triphenylvinyl)phenylboronic acid and 4,4'-(1,2-diphenylethene-1,2-diyl)bis(1,4-phenylene)diboronic acid generated TPETPy and TPE2TPy, respectively. The reaction intermediates and final products were fully characterized by spectroscopic methods from which satisfactory analysis data were obtained. Both TPETPy and TPE2TPy are soluble in acetonitrile, THF, and dimethylsulfoxide, slightly soluble in ethanol and methanol, but completely insoluble in water.

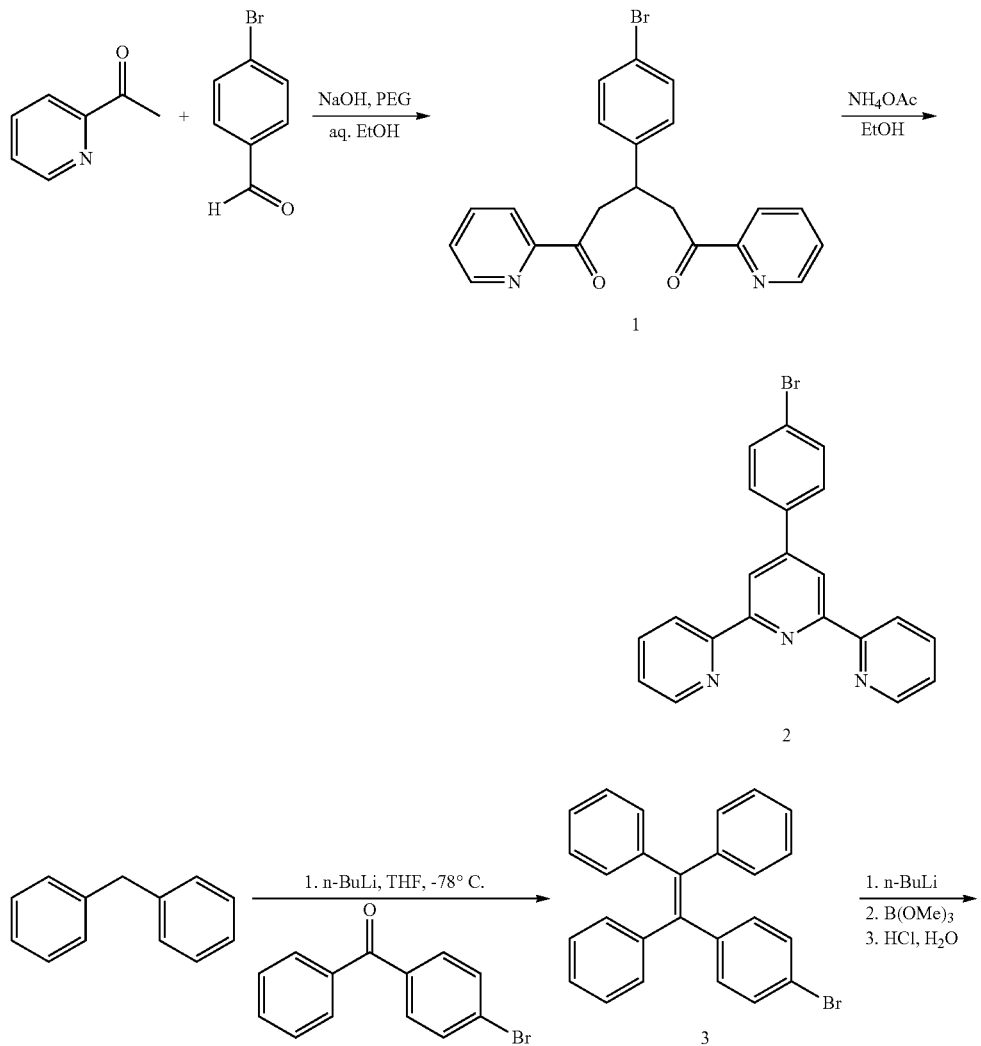

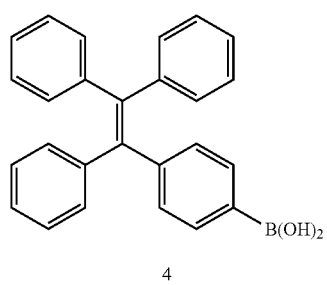

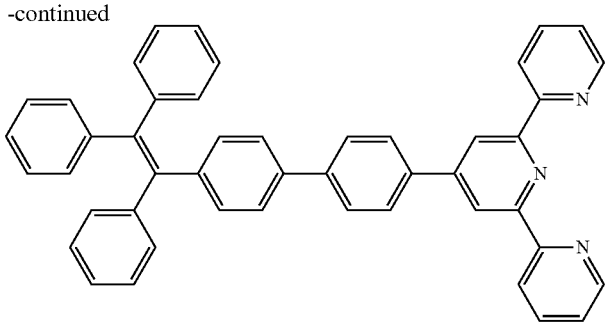

TPETPy

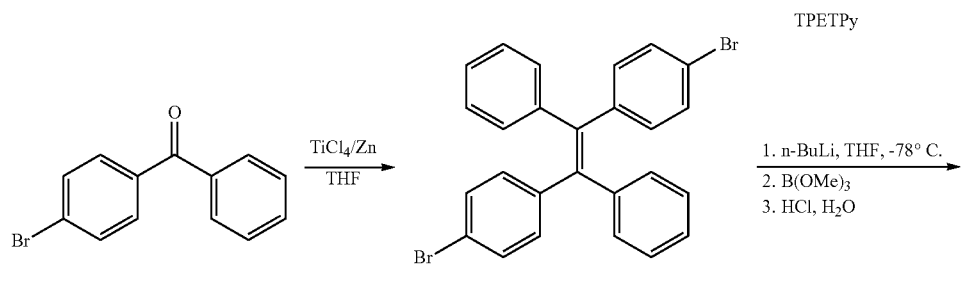

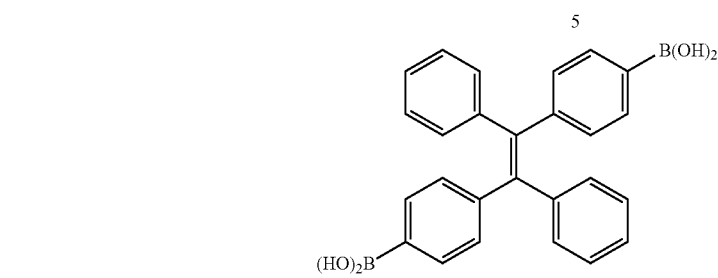

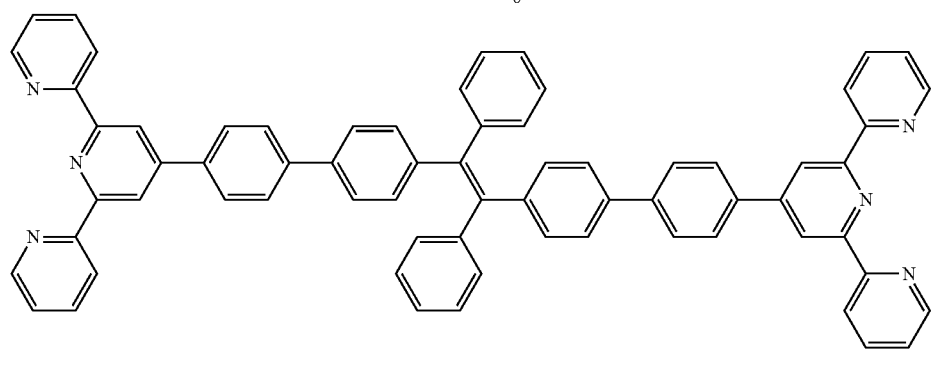

TPE2TPy

Example 1

Synthesis of 4'-(4-Bromophenyl)-2,2':6',2''-terpyridine (2)

2-acetylpyridine (5 g, 4.12 mmol) was added to a suspension of crushed NaOH (1.2 g, 8.25 mmol) in 70 mL of poly(ethylene glycol) (PEG, average molecular weight=300). After the solution was stirred at 0° C. for 10 min, 4-bromobenzaldehyde (3.76 g, 2.06 mmol) was then added by syringe and the suspension was kept at 0° C. for 2 h. Every 15 min, the suspension was manually stirred with a spatula as the viscosity became too great for adequate mixing using a magnetic stirrer. After 2 h, excess ammonium acetate (20 g) was added and the suspension was heated at 100° C. for 2 h. The color of the mixture changed from red to brown accompanied with the formation of fine brown precipitate. Water (150 mL) was added to the solution and the precipitate of 4'-(4-Bromophenyl)-2,2':6',2''-terpyridine (2) was isolated by filtration and washed with water (100 mL) and cold ethanol (20 mL). The crude product was purified on a basic aluminum oxide column using hexane/chloroform (1:1 v/v) as eluent. 4'-(4-Bromophenyl)-2,2':6',2''-terpyridine (2) was obtained as white powder in 75% yield (6.05 g). $^1$H NMR (400 MHz, CDCl$_3$), δ (ppm): 8.72 8.63 (m, 6H), 7.88 7.83 (m, 2H), 7.76 7.74 (d, 2H), 7.63 7.60 (d, 2H), 7.36 7.32 (m, 2H). $^{13}$C NMR (100 MHz, CDCl$_3$), δ (ppm): 156.0, 155.9, 149.1, 148.9, 137.3, 136.9, 132.0, 128.8, 123.9, 123.4, 121.3, 118.5. MS (TOF), m/e 388.0287 [(M+H)$^+$, calcd. 388.0371].

Example 2

Synthesis of 1-(4-bromophenyl)-1,2,2-triphenylethene (3)

To a solution of diphenylmethane (2.02 g, 12 mmol) in dry THF (20 mL) was added 4 mL of a 2.5 M solution of n-butyllithium in hexane (10 mmol) in an acetone-dry ice bath at −78° C. under nitrogen atmosphere. The resulting orange-red solution was stirred for 30 min at that temperature. To this solution was added 4-bromobenzophenone (9 mmol) and the reaction mixture was allowed to warm to room temperature with stifling for 6 h. The reaction was quenched with the addition of an aqueous solution of ammonium chloride, the organic layer was extracted with DCM, and the combined organic layers were washed with a saturated brine solution and dried over anhydrous $MgSO_4$. The solvent was evaporated, and the resulting crude alcohol was subjected to acid-catalyzed dehydration as follows.

The crude alcohol was dissolved in about 80 mL of toluene in a 100 mL Schlenk flask fitted with a Dean-Stark trap. A catalytic amount of p-toluenesulphonic acid (342 mg, 1.8 mmol) was added, and the mixture was refluxed for 3 4 h and cooled to room temperature. The toluene layer was washed with 10% aqueous $NaHCO_3$ solution, dried over anhydrous $MgSO_4$ and evaporated to afford the crude tetraphenylethylene derivative. The crude product was purified on a silica-gel column using hexane as eluent. 1-(4-bromophenyl)-1,2,2-triphenylethene (3) was isolated as intermediate in the reaction as a white solid in 93.6% yield. $^1H$ NMR (400 MHz, $CDCl_3$), δ (TMS, ppm): 7.21 (d, 2H), 7.09-7.14 (m, 9H), 6.99-7.03 (m, 6H), 6.88 (d, 2H). $^{13}C$ NMR ($CDCl_3$, 100 MHz) δ (ppm): 126.4, 126.63, 126.69, 127.0, 127.3, 127.85, 127.90, 127.96, 128.9, 131.55, 131.63, 132.0, 139.0, 140.7, 140.8, 141.3, 143.0, 143.93, 143.97.

Example 3

Synthesis of 4-(1,2,2-Triphenylvinyl)phenylboronic acid (4)

Into a 250 mL two-necked round-bottom flask under nitrogen was slowly added n-butyllithium (1.6 M in hexane, 7.5 mL, 12 mmol) and a THF solution (80 mL) of 1-(4-bromophenyl)-1,2,2-triphenylethene (3) (4.11 g, 10 mmol) at −78° C. After stirring for 3 h, 2.4 mL of trimethylborate (20 mmol) was added into the reaction mixture. The mixture was warmed to room temperature and the reaction was terminated by adding hydrochloric acid (2 M, 10 mL) after 12 h. The mixture was then poured into water and extracted with dichloromethane. The organic layer was washed with water and dried over magnesium sulfate. After filtration and solvent evaporation, the residue was purified by silica-gel column chromatography using n-hexane/ethyl acetate as eluent. White solid of 4-(1,2,2-Triphenylvinyl)phenylboronic acid (4) was obtained in 70% yield (2.6 g). $^1H$ NMR (300 MHz, $CDCl_3$), δ (TMS, ppm): 7.88 (d, 2H, J=8.1 Hz), 7.13-7.00 (m, 17H), 4.49 (s, 1H). $^{13}C$ NMR (75 MHz, $CDCl_3$), δ (TMS, ppm): 148.9, 144.2, 144.1, 144.09, 142.4, 141.4, 135.6, 133.5, 132.0, 131.6, 128.4, 128.3, 127.4, 127.2. HRMS (TOF): m/e 376.2030 ($M^+$, calcd 376.1635).

Example 4

Synthesis of 1-[4'-(4'-2,2':6',2''-Terpyridyl)-biphenyl-4-yl]-1,2,2-triphenylethene (TPETPy)

4-(1,2,2-Triphenylvinyl)phenylboronic acid (4) (0.3 g, 0.71 mmol), 4'-(4-Bromophenyl)-2,2':6',2''-terpyridine (2) (0.5 g, 1.43 mmol), and tetrakis(triphenylphosphine)palladium(0) (41 mg, 0.036 mmol) were dissolved in 30 mL of degassed THF. 3 mL of saturated aqueous $Na_2CO_3$ solution was added to the mixture under stirring. After reflux for 48 h, the reaction mixture was cooled to room temperature and filtered. The solvent was evaporated under vacuum and the organic solution was washed with water three times. The crude product was purified on a basic aluminium oxide column using hexane/chloroform (1:1 v/v) as eluent. TPETPy was obtained as yellow powder in 48% yield (0.2 g). $^1H$ NMR (400 MHz, $CDCl_3$), δ (ppm): 8.78 (s, 2H), 8.72 8.66 (m, 8H), 7.95 7.93 (d, 2H), 7.85 7.82 (m, 4H), 7.74 7.60 (t, 5H), 7.45 7.43 (d, 2H), 7.33 7.30 (m, 4H), 7.17 7.11 (m, 4H), 7.03 7.01 (m, 2H). $^{13}C$ NMR (100 MHz, $CDCl_3$), δ (ppm): 156.0, 155.7, 151.4, 149.4, 148.9, 148.7, 143.5, 142.9, 141.1, 141.0, 140.3, 137.8, 137.1, 136.8, 136.6, 135.7, 131.9, 131.7, 131.3, 131.2, 128.6, 128.1, 127.7, 127.5, 127.4, 127.1, 126.4, 126.3, 126.0, 125.4. HRMS (TOF), m/e 639.1811 ($M^+$, calcd. 639.2674).

Example 5

Synthesis of 1,2-Bis(4-bromophenyl)-1,2-diphenylethene (5)

In a suspension of 4-bromobenzophenone (5 g, 19.2 mmol) in 50 mL of THF were added $TiCl_4$ (2.14 mL, 19.2 mmol) and Zn dust (2.48 g, 38.4 mmol). After reflux for 20 h, the reaction mixture was cooled to room temperature and filtered. The solvent was evaporated under vacuum and the crude product was purified by a silica gel column using hexane as eluent. 1,2-Bis(4-bromophenyl)-1,2-diphenylethene (5) was obtained as white solid in 95% yield (4.3 g). $^1H$ NMR ($CDCl_3$, 300 MHz), δ (ppm): 7.27 7.19 (m, 4H), 7.15 7.09 (m, 6H), 6.98 (m, 4H), 6.90 6.86 (m, 4H). $^{13}C$ NMR ($CDCl_3$, 75 MHz), δ (TMS, ppm): 133.0, 131.3, 131.2, 131.0, 128.1, 127.9, 127.8, 127.0, 126.9. MS (TOF): m/e 489.9 ($M^+$, calcd 490.0).

Example 6

Synthesis of 4,4'-(1,2-Diphenylethene-1,2-diyl)bis(1,4-phenylene)diboronic acid (6)

1,2-Bis(4-bromophenyl)-1,2-diphenylethene (5) (0.4 g, 0.82 mmol) was dissolved in 20 mL of THF in a 100 mL flask. The flask was cooled in an acetone-dry ice bath at −78° C. and 1.0 mL (2.6 mmol) of n-butyllithium (2.5 M in hexane) was added carefully. After stifling for 1 h, 0.46 mL (4.0 mmol) of trimethyl borate was added and the mixture was allowed to react for 45 min. The mixture was warmed to room temperature and stirred overnight. Dilute HCl solution was then added to quench the reaction. After filtration and solvent evaporation, the product was purified by silica gel column using ethyl acetate as eluent. The product was obtained as yellow solid in 54% yield. $^1H$ NMR ($CD_3OD$, 300 MHz) δ (ppm): 7.26 7.17 (m, 10H), 7.01 6.94 (m, 4H), 6.73 6.65 (m, 4H). $^{13}C$ NMR ($CD_3OD$, 75 MHz), δ (TMS, ppm): 157.2, 146.2, 141.4, 137.0, 133.9, 132.7, 128.9, 127.4, 115.7. MS (TOF): m/e 422.2 [$(M)^+$, calcd: 422.1].

Example 7

Synthesis of 1,2-Bis[4'-(4'-2,2':6',2''-terpyridyl)-biphenyl-4-yl]-1,2-diphenylethene (TPE2TPy)

4,4'-(1,2-Diphenylethene-1,2-diyl)bis(1,4-phenylene)diboronic acid (6) (0.3 g, 0.71 mmol), 4'-(4-Bromophenyl)-2,2':6',2''-terpyridine (2) (0.5 g, 1.43 mmol), and tetrakis(triphenylphosphine)palladium(0) (41 mg, 0.036 mmol) were dissolved in 30 mL of degassed THF. 3 mL of saturated aqueous $Na_2CO_3$ solution was added to the mixture under stirring. After reflux for 48 h, the reaction mixture was cooled to room temperature and filtered. The solvent was evaporated under vacuum and the organic solution was washed with water three times. The crude product was purified on a basic aluminium oxide column using hexane/chloroform (1:1 v/v) as eluent. TPE2TPy was obtained as yellow powder in 52% yield (0.37 g). $^1$H NMR (400 MHz, $CDCl_3$), δ (ppm): 8.76 8.74 (m, 8H), 8.68 8.66 (m, 4H), 8.05 8.01 (t, 4H), 8.00 7.97 (d, 2H), 7.86 7.84 (m, 4H), 7.63 7.61 (m, 4H), 7.57 7.51 (m, 6H), 7.20 7.15 (m, 4H), 7.12 7.10 (m, 4H), 7.05 7.04 (m, 4H). $^{13}$C NMR (100 MHz, $CDCl_3$), δ (ppm): 156.1, 149.1, 143.4, 136.9, 132.0, 128.6, 127.5, 126.2, 123.9, 121.4, 118.6, 118.5. HRMS (TOF): m/e 947.3715 (M$^+$, calcd. 947.1330).

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

We claim:

1. A fluorescent sensor for metal ions comprising a luminogen that exhibits aggregation induced emission properties functionalized with a terpyridine moiety; wherein the luminogen functionalized with terpyridine moiety comprises a backbone structure selected from the group consisting of:

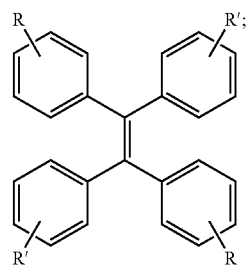

wherein R and R' are independently selected from the group consisting of H and (X)—R";
wherein X is selected from the group consisting of $(Ph)_n$,
wherein n=0 to 20;

wherein R" is

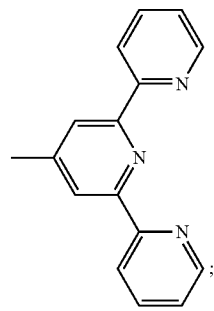 [SMILES: Cc1cc(-c2ccccn2)nc(-c2ccccn2)c1]

wherein the backbone structure must have at least one R" group present; and
wherein the luminogen functionalized with the terpyridine moiety is 1-[4'-(4'-2,2':6',2''-Terpyridyl)-biphenyl-4-yl]-1,2,2-triphenylethene (TPETPy), having the structure

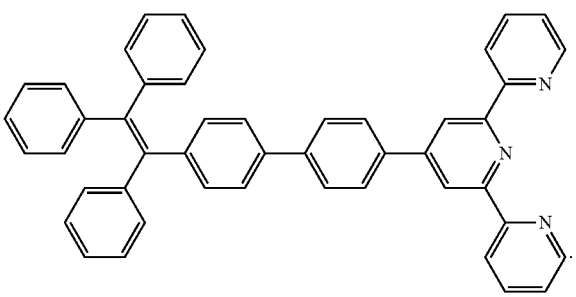 [SMILES: c1ccc(C(=C(c2ccccc2)c2ccc(-c3ccc(-c4cc(-c5ccccn5)nc(-c5ccccn5)c4)cc3)cc2)c2ccccc2)cc1]

2. The fluorescent sensor for metal ions of claim 1, wherein the metal ion is selected from the group consisting of zinc, iron, copper, cadmium, and mercury ions.

3. The fluorescent sensor for metal ions of claim 2, wherein the metal ion is zinc ion.

4. The fluorescent sensor for metal ions of claim 1, wherein the luminogen functionalized with the terpyridine moiety forms a complex with a metal ion which intensifies the fluorescence of the fluorescent sensor for metal ions.

5. The fluorescent sensor for metal ions of claim 4, wherein the metal ion is selected from the group consisting of zinc, iron, copper, cadmium, and mercury ions.

6. The fluorescent sensor for metal ions of claim 5, wherein the metal ion is zinc ion.

7. A method of detecting and identifying a metal ion in a sample comprising:
  (a) contacting the sample with the fluorescent sensor for metal ions of claim 1,
  (b) detecting fluorescence,
  (c) measuring the fluorescence emission intensity, and
  (d) identifying the metal ion based on any spectral shift signaling or intensity change of the fluorescence emission intensity.

8. The method of claim 7, wherein the fluorescent sensor for metal ions forms a complex with the metal ion which intensifies the fluorescence of the fluorescent sensor for metal ions.

9. The method of claim 8, wherein the metal ion is selected from the group consisting of zinc, iron, copper, cadmium, and mercury ions.

10. The method of claim 9, wherein the metal ion is zinc ion.

11. A method of detecting and identifying a metal ion in a sample comprising:
   (a) contacting the sample with the fluorescent sensor for metal ions of claim 4,
   (b) detecting fluorescence,
   (c) measuring the fluorescence emission intensity, and
   (d) identifying the metal ion based on any spectral shift signaling or intensity change of the fluorescence emission intensity.

12. The method of claim 11, wherein the fluorescent sensor for metal ions forms a complex with the metal ion which intensifies the fluorescence of the fluorescent sensor for metal ions.

13. The method of claim 12, wherein the metal ion is selected from the group consisting of zinc, iron, copper, cadmium, and mercury ions.

14. The method of claim 13, wherein the metal ion is zinc ion.

* * * * *